United States Patent
Paolitto et al.

(10) Patent No.: US 9,089,424 B2
(45) Date of Patent: Jul. 28, 2015

(54) AORTIC ANNULOPLASTY RING

(71) Applicant: Coroneo, Inc., Montreal (CA)

(72) Inventors: Anthony Paolitto, St-Leonard (CA); Valerio Valentini, Montreal (CA)

(73) Assignee: CORONEO, INC., Montreal (CA)

( * ) Notice: Subject to any disclaimer, the term of this patent is extended or adjusted under 35 U.S.C. 154(b) by 0 days.

(21) Appl. No.: 14/265,476

(22) Filed: Apr. 30, 2014

(65) Prior Publication Data

US 2014/0236290 A1   Aug. 21, 2014

Related U.S. Application Data

(63) Continuation of application No. 13/227,999, filed on Sep. 8, 2011, now Pat. No. 8,734,506, which is a continuation of application No. 11/183,939, filed on Jul. 19, 2005, now Pat. No. 8,034,102.

(60) Provisional application No. 60/588,745, filed on Jul. 19, 2004.

(51) Int. Cl.
*A61F 2/24* (2006.01)
*A61F 2/06* (2013.01)

(52) U.S. Cl.
CPC ............. *A61F 2/2442* (2013.01); *A61F 2/2445* (2013.01); *A61F 2/06* (2013.01)

(58) Field of Classification Search
CPC .............................. A61F 2/2442; A61F 2/2445
USPC .......................................... 623/2.1, 2.36, 2.37
See application file for complete search history.

(56) References Cited

U.S. PATENT DOCUMENTS

| | | |
|---|---|---|
| 3,570,014 A | 3/1971 | Hancock |
| 3,714,671 A | 2/1973 | Edwards et al. |
| 3,755,823 A | 9/1973 | Hancock |
| 3,983,581 A | 10/1976 | Angell et al. |
| 4,106,129 A | 8/1978 | Carpentier et al. |
| 4,343,048 A | 8/1982 | Ross et al. |
| 4,441,216 A | 4/1984 | Ionescu et al. |

(Continued)

FOREIGN PATENT DOCUMENTS

| | | |
|---|---|---|
| WO | 9746177 A1 | 12/1997 |
| WO | 2005055883 A1 | 6/2005 |

OTHER PUBLICATIONS

Duran et al., New prosthetic ring for aortic valve annuloplasty, CardioVascular Surgery, Apr. 1993, vol. 1, No. 2, pp. 166-171.

*Primary Examiner* — Howie Matthews
(74) *Attorney, Agent, or Firm* — Wood, Herron & Evans, L.L.P.

(57) ABSTRACT

An annuloplasty ring to resize a dilated aortic root during valve sparing surgery includes a scalloped space frame having three trough sections connected to define three crest sections. The annuloplasty ring is mounted outside the aortic root, and extends in height between a base plane and a spaced apart commissure plane of the aortic root. At least two adjacent trough sections are coupled by an annulus-restraining member or tether that limits the maximum deflection of the base of the annuloplasty ring. In use, the tether is preferably located in proximity to the base plane of the aortic root. The annuloplasty ring is movable between a first, substantially conical configuration occurring during a diastolic phase of the cardiac cycle, and a second, substantially cylindrical configuration occurring during a systolic phase of the cardiac cycle.

4 Claims, 21 Drawing Sheets

(56) References Cited

U.S. PATENT DOCUMENTS

| | | |
|---|---|---|
| 4,851,000 A | 7/1989 | Gupta |
| 5,163,953 A | 11/1992 | Vince |
| 5,258,021 A | 11/1993 | Duran |
| 5,360,444 A | 11/1994 | Kusuhara |
| 5,376,112 A | 12/1994 | Duran |
| 5,469,868 A | 11/1995 | Reger |
| 5,489,297 A | 2/1996 | Duran |
| 5,545,215 A | 8/1996 | Duran |
| 5,549,665 A | 8/1996 | Vesely et al. |
| 5,584,879 A | 12/1996 | Reimold et al. |
| 5,607,471 A | 3/1997 | Seguin et al. |
| 5,728,152 A | 3/1998 | Mirsch, II et al. |
| 6,231,602 B1 | 5/2001 | Carpentier et al. |
| 6,248,116 B1 | 6/2001 | Chevillon et al. |
| 6,258,122 B1 | 7/2001 | Tweden et al. |
| 6,264,691 B1 | 7/2001 | Gabbay |
| 6,348,068 B1 | 2/2002 | Campbell et al. |
| 6,350,282 B1 | 2/2002 | Eberhardt |
| 6,478,819 B2 | 11/2002 | Moe |
| 6,558,418 B2 | 5/2003 | Carpentier et al. |
| 6,635,085 B1 | 10/2003 | Caffey et al. |
| 6,997,951 B2 | 2/2006 | Solem et al. |
| 7,011,681 B2 | 3/2006 | Vesely |
| 2005/0065597 A1 | 3/2005 | Lansac |
| 2005/0165478 A1 | 7/2005 | Song |

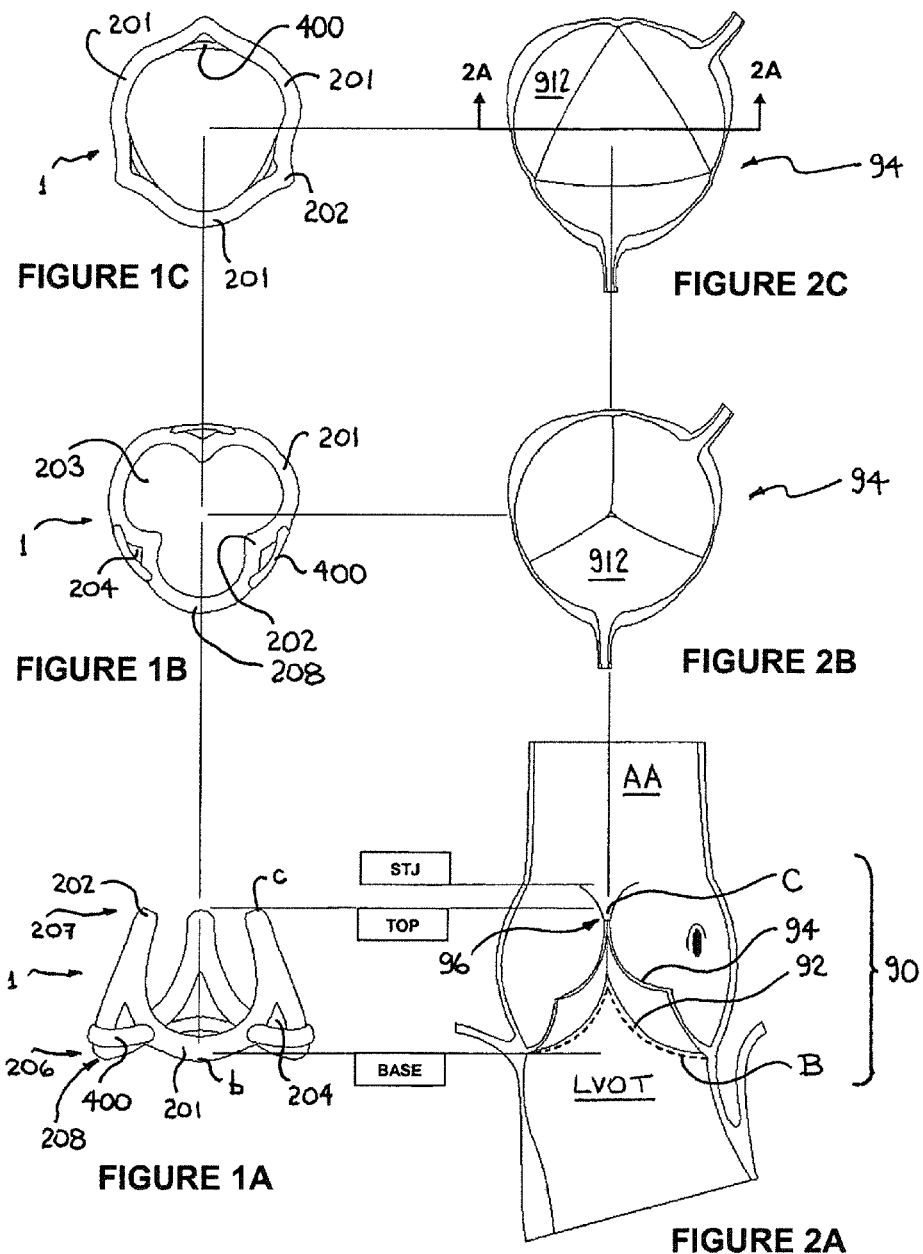

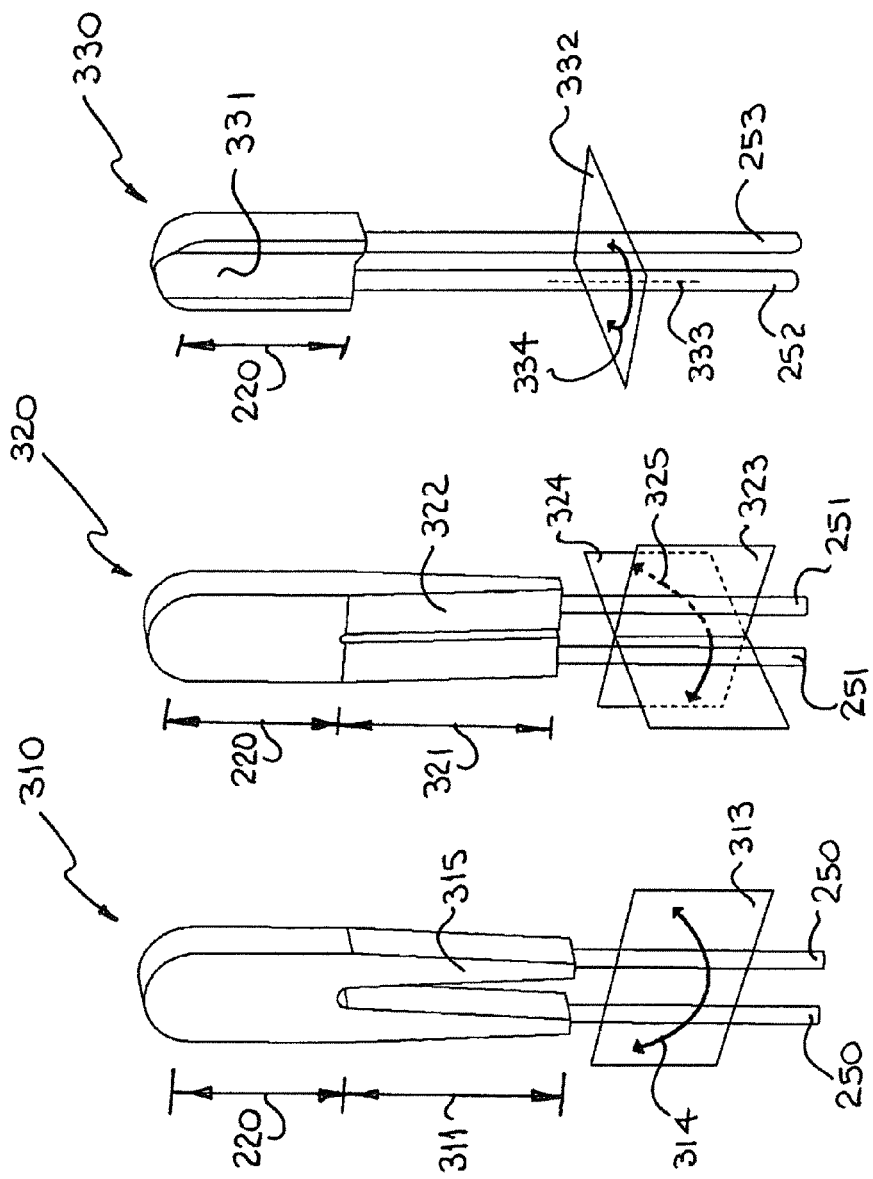

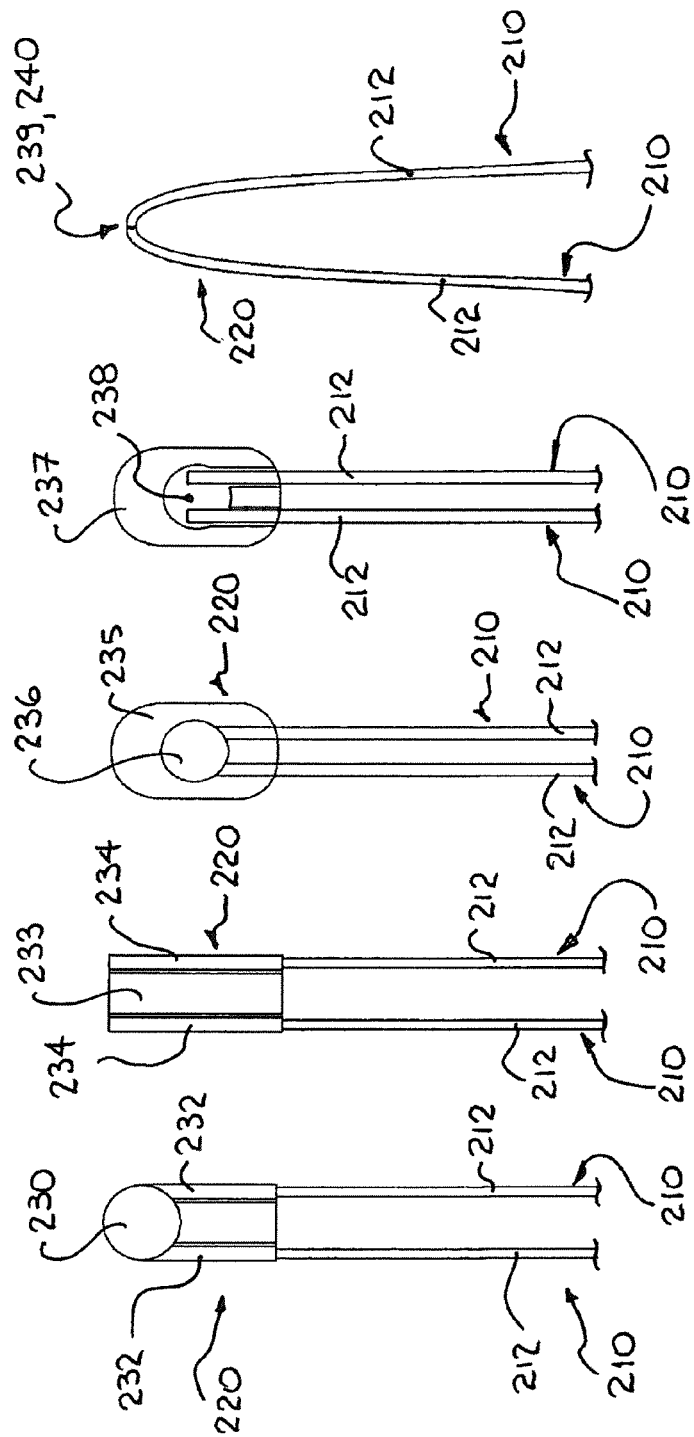

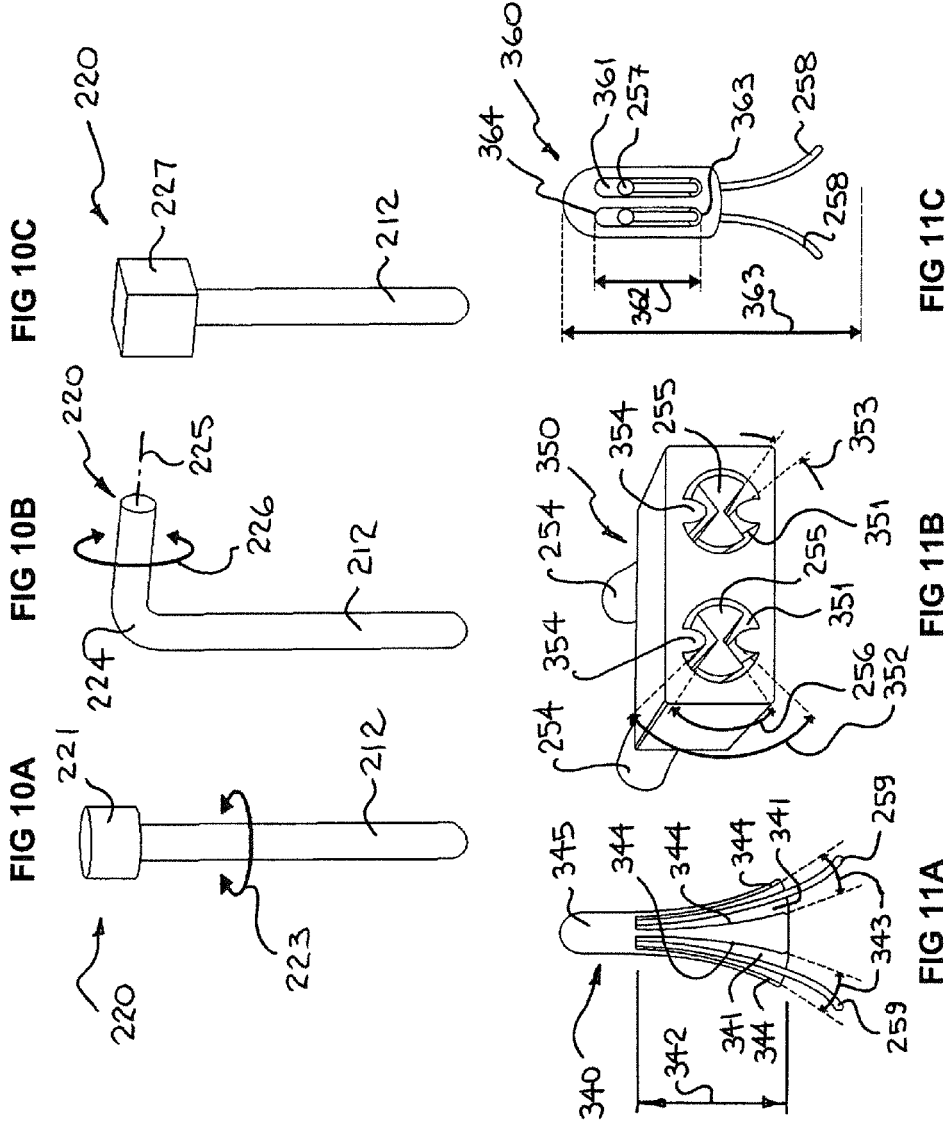

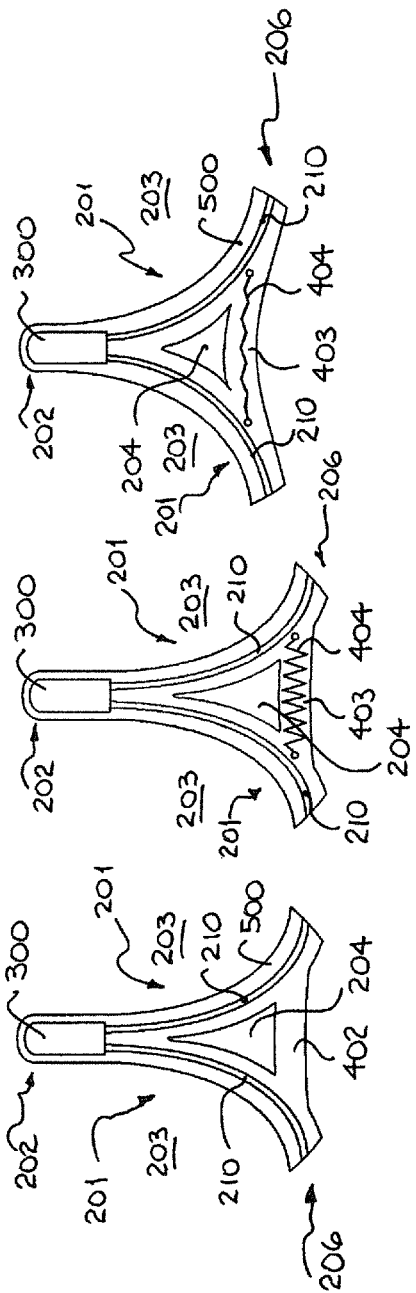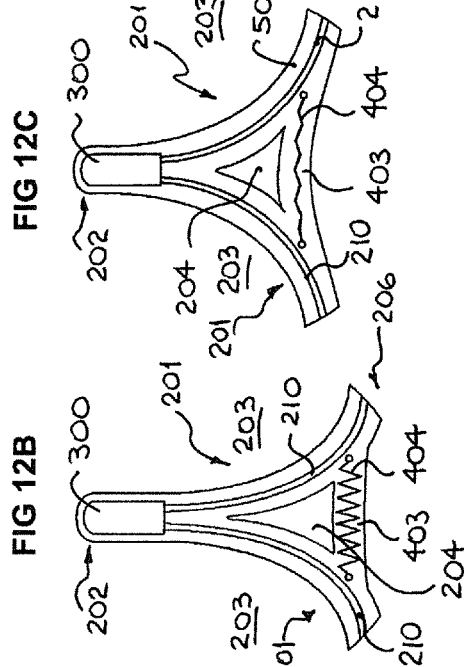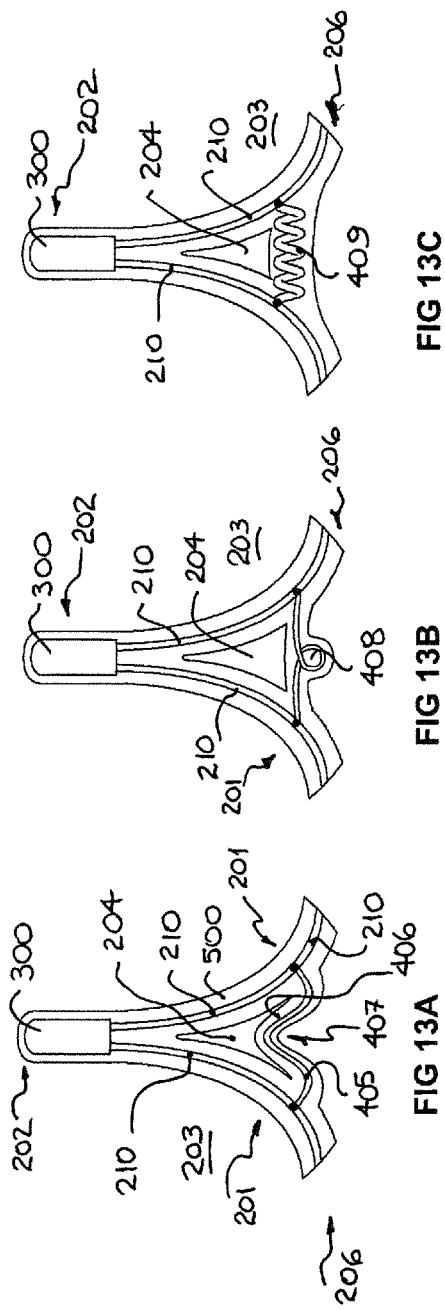

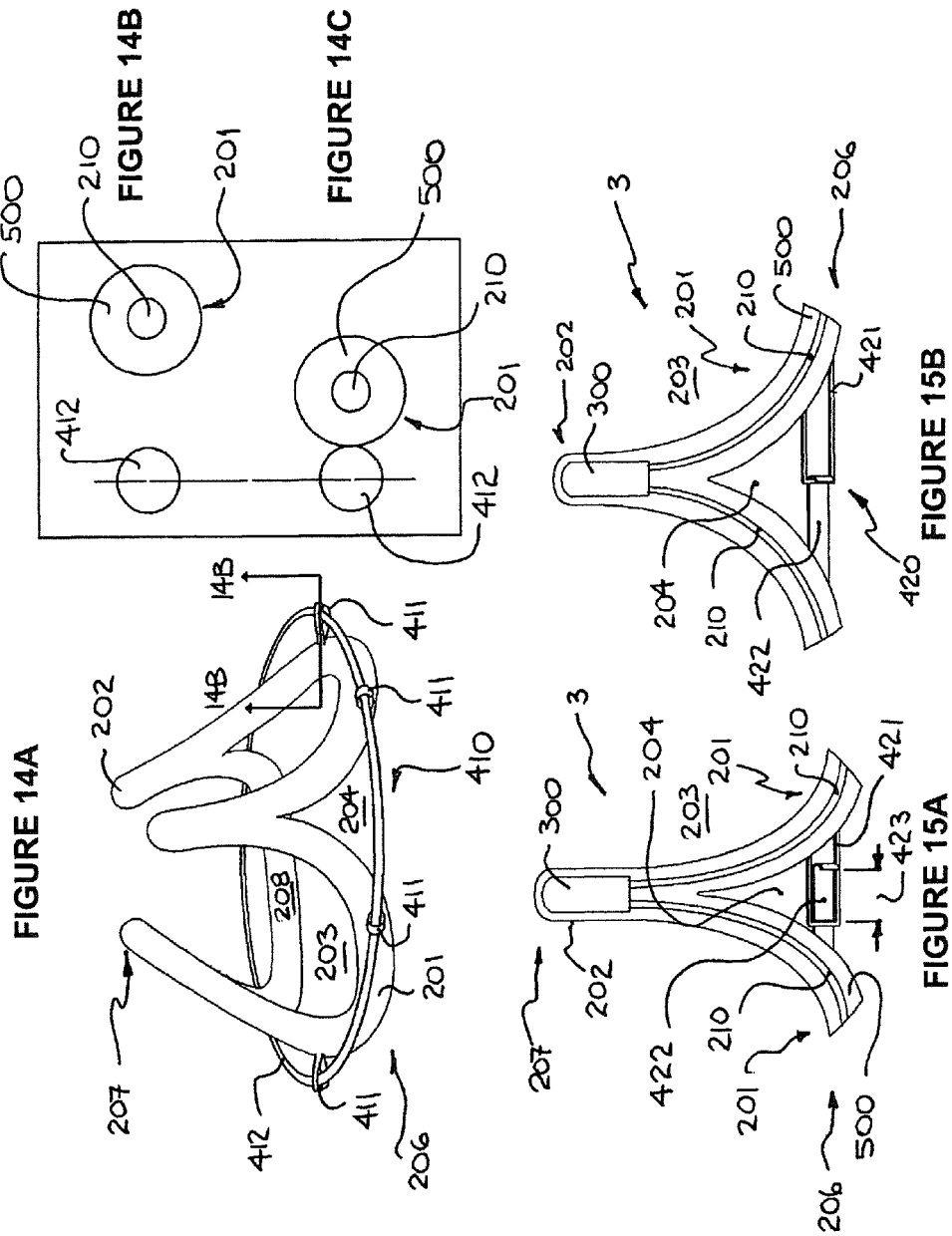

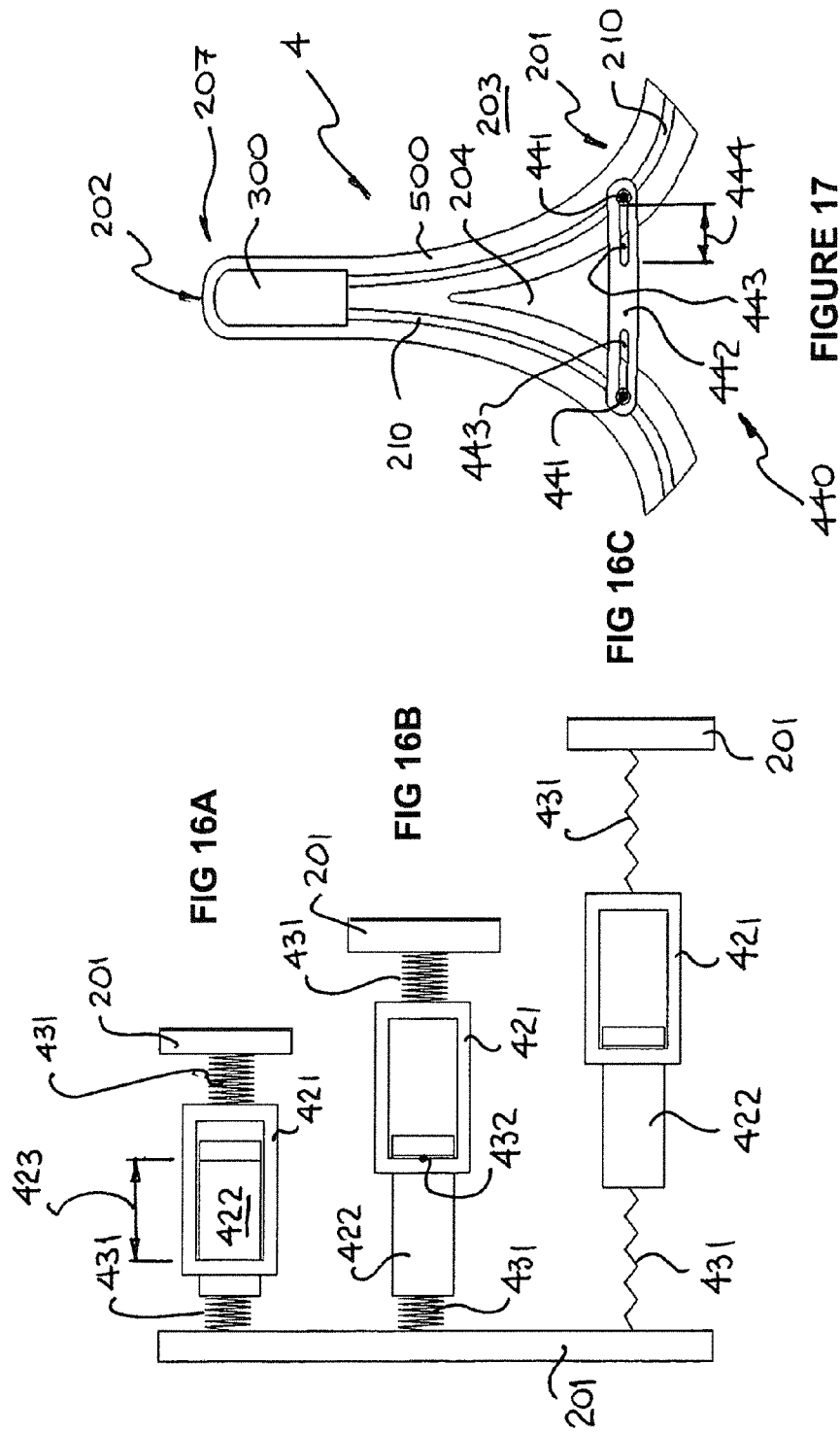

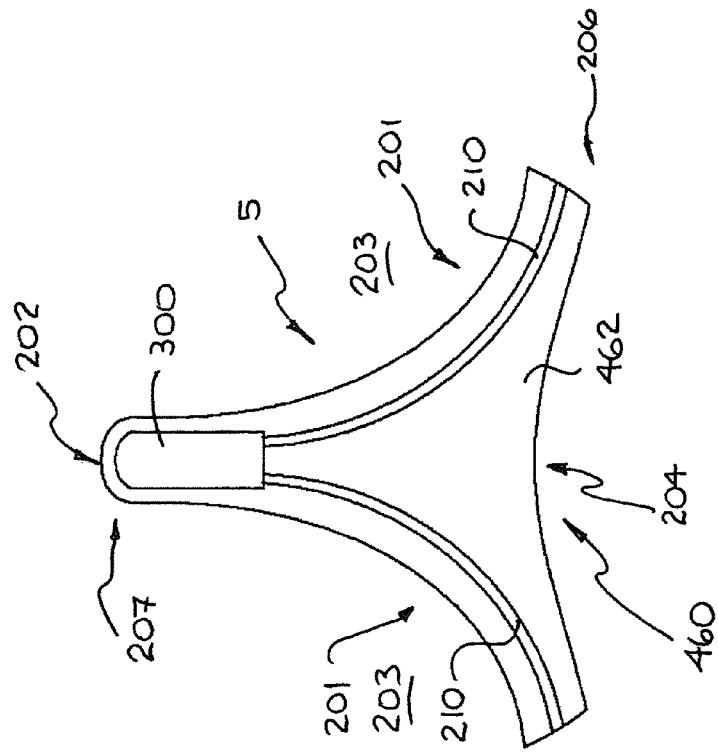
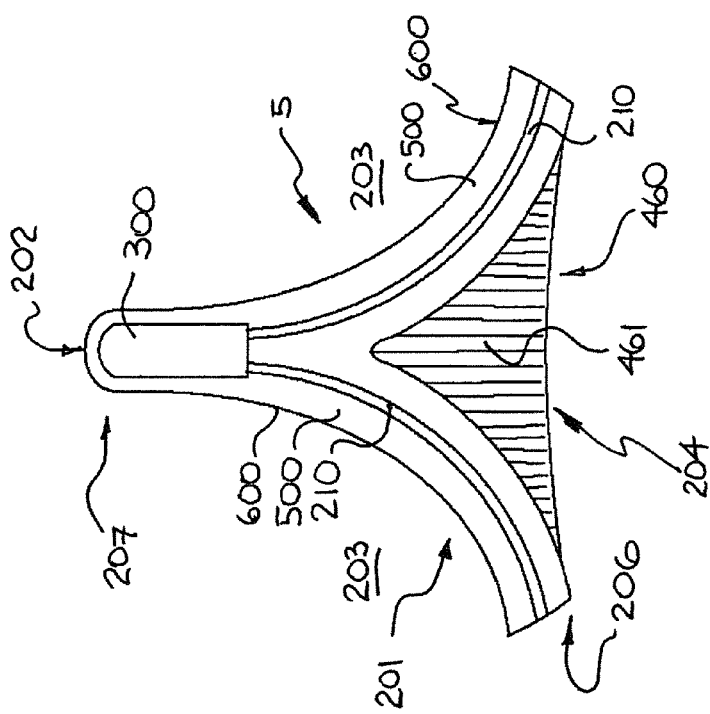
FIGURE 18A
FIGURE 18B

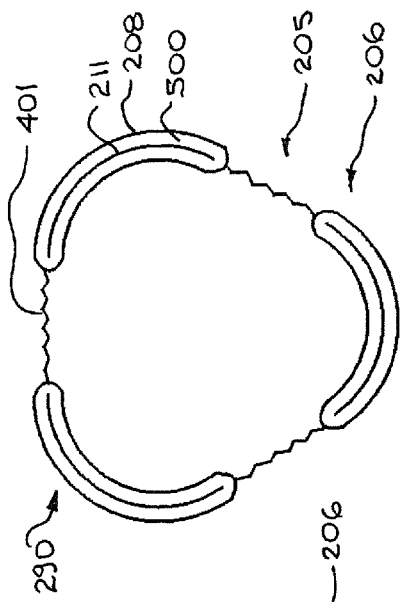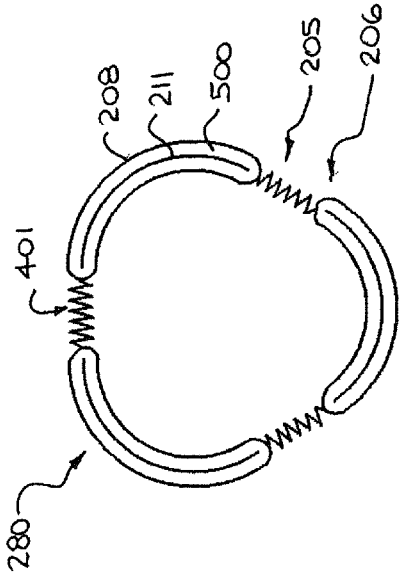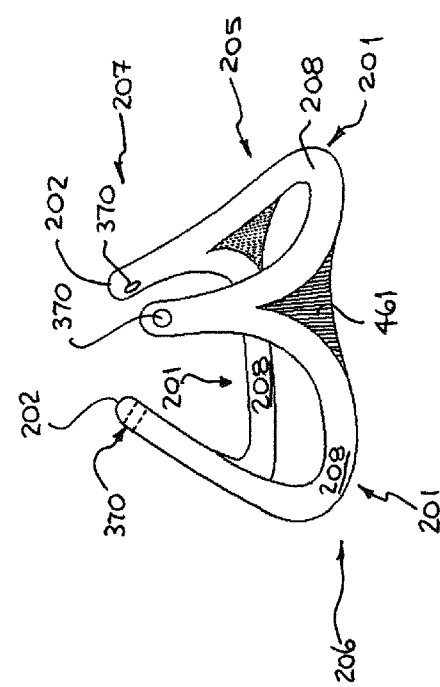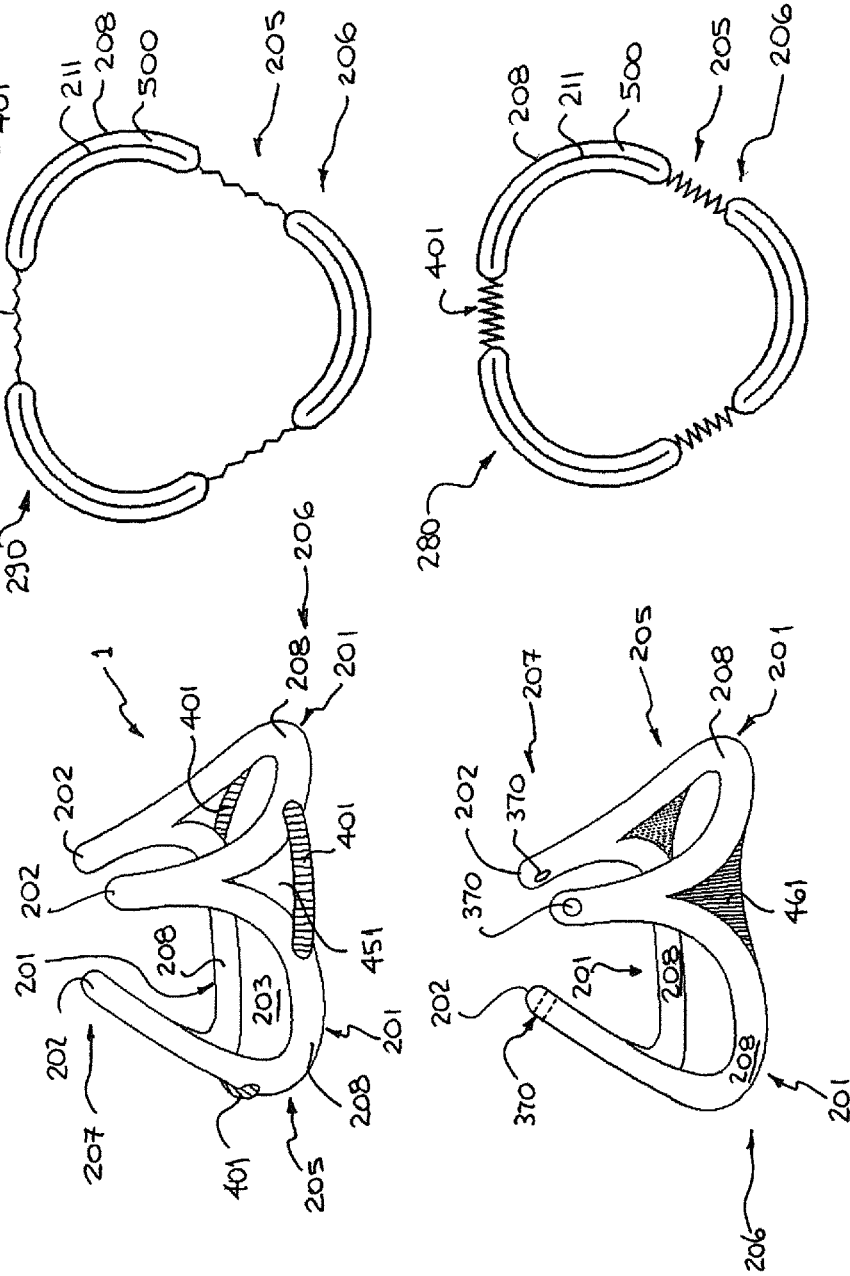

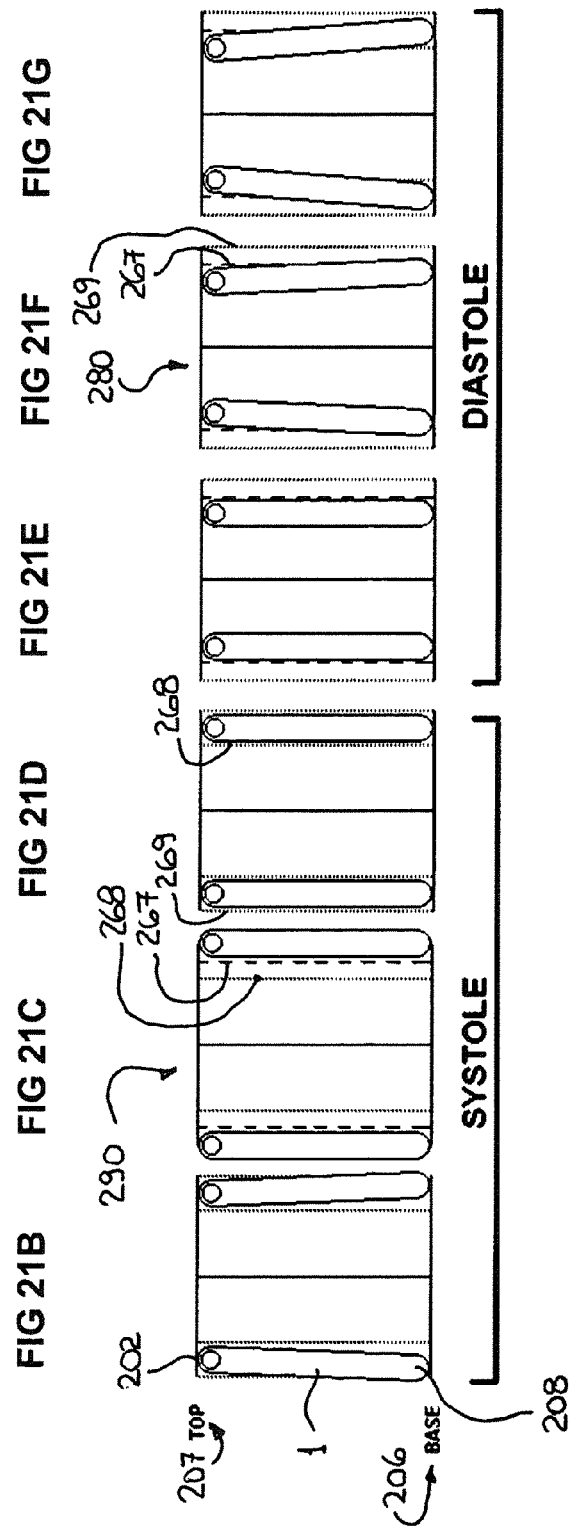

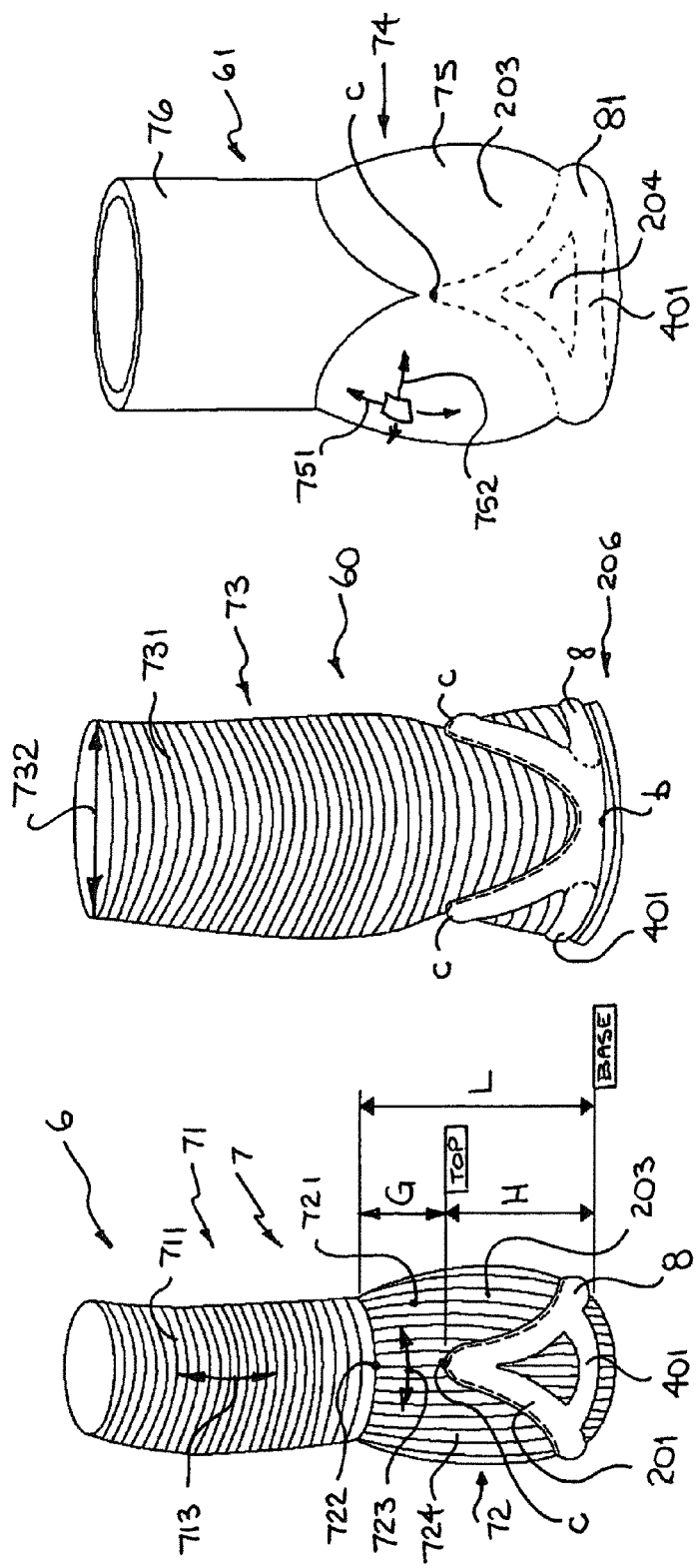

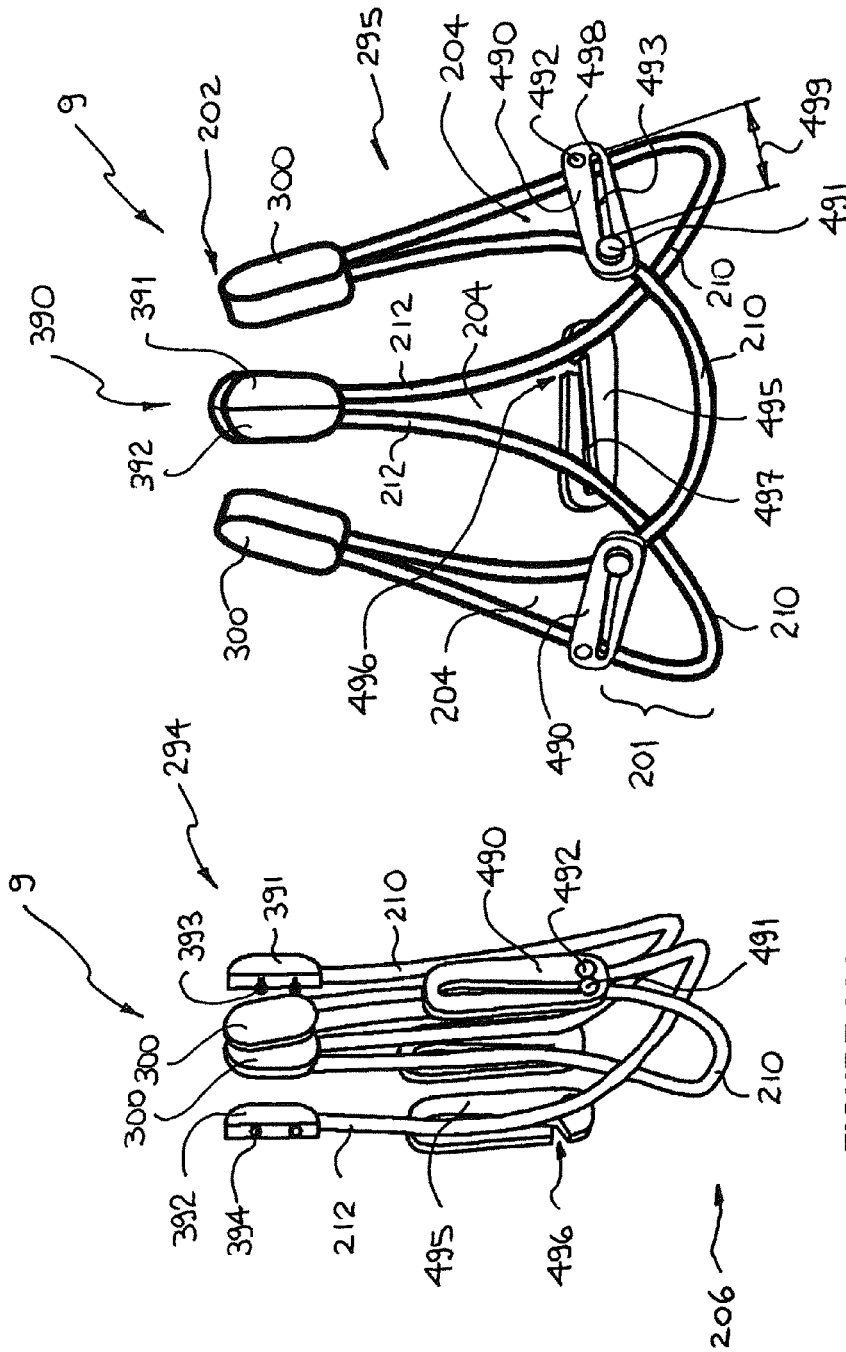

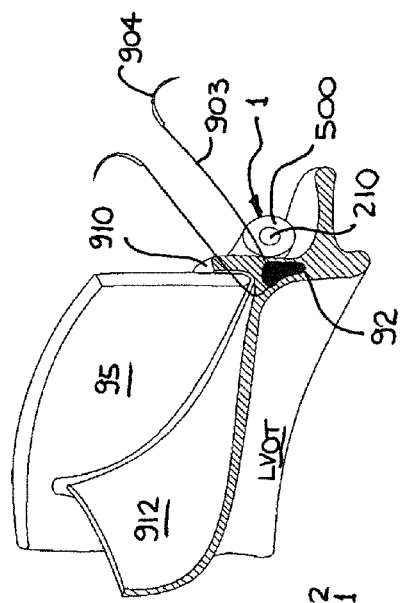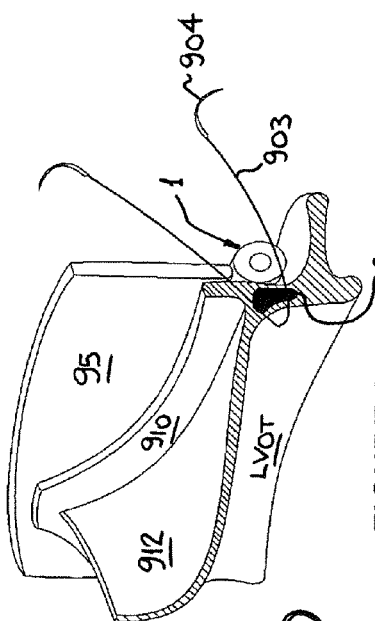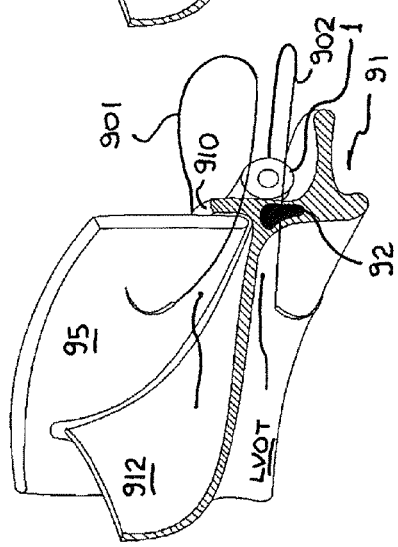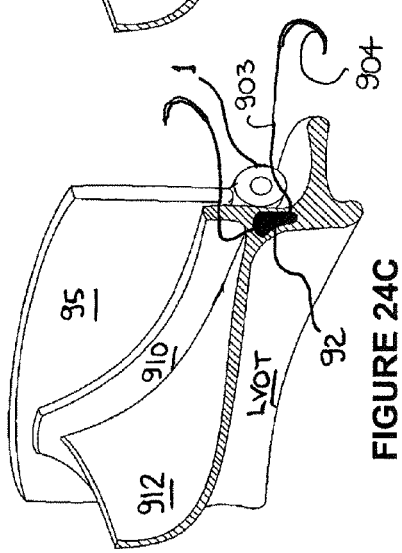

"DAVID – REIMPLANTATION"

"YACOUB – REMODELING"

AORTIC ANNULOPLASTY RING

CROSS-REFERENCE TO RELATED APPLICATION

This application is a continuation of application Ser. No. 13/227,999, filed Sep. 8, 2011 (now U.S. Pat. No. 8,734,506) which is a continuation of application Ser. No. 11/183,939, filed Jul. 19, 2005 (now U.S. Pat. No. 8,034,102) which claims the benefit of U.S. Provisional Patent Application Ser. No. 60/588,745 filed on Jul. 19, 2004, the disclosures of which are hereby incorporated by reference herein.

FIELD OF THE INVENTION

The present invention relates to the general field of implantable cardiac devices, and is particularly concerned with annuloplasty devices that may be used to correct valvular insufficiency in valve-sparing procedures.

BACKGROUND OF THE INVENTION

Aortic root dilation is one of the most common causes of aortic valve incompetence in North America. Prevalence of surgical corrections for this pathology has increased considerably during the last two decades. Mechanisms involved in this pathology have been experimentally and clinically studied resulting in a variety of surgical corrections. While some of the surgical corrections are better adapted to the aortic physiology, others, less convenient, have been associated with recurrent aortic disease and valvular insufficiency. There is room for improvement in providing a surgical correction that respects the normal aortic root physiology in the correction of aortic valve insufficiency associated to aortic annuloectasia, aortic aneurysm and other such dilatations.

As is well known, the mammalian heart is an organ made up of four muscular chambers that function together to pump blood throughout the body. Each of the four chambers has an associated downstream one-way valve made up of movable, coapting leaflets or cusps which cooperate to prevent the backward flow of blood, or regurgitation, into their respective chambers. Two such heart valves, the aortic and pulmonary valves, also commonly known as the semilunar valves, are characterized by three leaflets or cusps. The aortic valve leaflets are attached within the aortic root, to a tri-scalloped or triple scalloped line of collagenous, fibrous tissue generally referred to as the valve annulus. As such, a three-pointed crown-like structure serves to support the aortic valve cusps or leaflets. The U-shaped convex lower edges of each leaflet are attached to, and suspended from, the base of the aortic root, with the upper free edges or margins of each leaflet being free to move and project into the lumen of the aorta. Two adjacent leaflets approach one another at one of the three points of said crown-like structure to define a commissure of the aortic valve. Behind each leaflet, the aortic vessel wall bulges outward, forming a pouch-like dilatation known as the sinus of Valsalva. In the region located slightly above the level of the commissures, the aortic root creating the sinuses of Valsalva merges into the substantially tubular portion of the ascending aorta at a substantially planar transition zone commonly known as the sinotubular junction (STJ). The aortic root houses the aortic valve structure and generally includes the portion of the native aortic conduit extending from the left ventricular outflow tract (LVOT) to the portion of ascending aorta (AA) slightly above the sinotubular junction. Typically, aortic root reconstructions or interventions usually involve the aortic valve, while ascending aorta interventions usually exclude the aortic valve and involve the native aortic conduit located generally downstream of the sinotubular junction.

During ventricular systole, the leaflets are passively thrust upward and outwardly away from the centre of the aortic lumen, while in a synchronous manner, the commissures move out radially with the aortic root. As such, the free edges of the leaflets are no longer in contact with each other as they assume a triangular geometric relationship when viewed along the axis of the aortic lumen. This may also be referred to as triangulation of the valve leaflets (FIG. 2C). During ventricular diastole, the leaflets fall passively into the lumen of the aorta, and coapt at their respective free edges to support the column of blood above. In a synchronous manner, the commissures move radially inward with the aortic root, thereby allowing the free edges to resume contact with each other and assume a Y-shaped geometric relationship (FIG. 2B). This may also be referred to as coaptation of the valve leaflets. In a healthy aortic valve, the geometry of the leaflets and the strong fibrous tissue support thereof provide excellent approximations of the leaflets and prevent regurgitation of flow through the aortic valve. In a diseased aorta, the dilatation of the aortic root or valve annulus, or the aneurysm of the aortic wall, results in compromised leaflet coaptation leading to regurgitation and valve insufficiency.

The aortic valve is a critical component in maintaining adequate flow of oxygenated blood to the rest of the body. The conduit downstream of the aortic valve, generally above the sinotubular junction, is known as the ascending aorta. A number of diseases lead to dilatation of the aortic root structure and aortic valve annulus, also called aneurysm or ectasia, which in turn affects the ability of the aortic valve leaflets to coapt or close completely. This ensuing condition, known as aortic insufficiency, can severely diminish the heart's ability to effectively deliver blood to the rest of the body or to the heart muscle, and can lead to serious complications and death.

Until the early 1990s, a common treatment for managing aortic insufficiency caused by aortic root dilatation consisted of completely resecting the aortic valve and aortic root, and replacing such native structures with a composite heart valve—aortic root prosthesis (i.e., an aortic valved conduit). One of the drawbacks of this surgical intervention, known as the Bentall procedure, is that in patients having relatively healthy leaflets, such leaflets are sacrificed and replaced by a prosthetic valve in order to correct the aortic dilatation. In addition, there is a need for prolonged anti-coagulation therapy in the case of Bentall procedures using mechanical heart valves, and a risk of valve degradation and reoperation in the case of Bentall procedures using bioprosthetic heart valves.

Some of the problems associated with a Bentall procedure have been addressed through the development of a surgical procedure known as aortic valve-sparing, in which the aortic root is resected above the aortic annulus, leaving a scalloped portion of native tissue, or fringe, extending slightly above the leaflets. From approximately the same starting point, two valve-sparing procedures have evolved. The first, known as reimplantation (FIG. 26A), involves the placement of a Dacron root prosthesis or synthetic aortic conduit over the scalloped native tissue, where it is sutured both below the valve leaflets through the valve annulus, and above the valve leaflets. The procedure is generally long and difficult to perform, and often results in leaflet impact or concussion with the walls of the Dacron prosthesis during the ejection phase of the cardiac cycle. In addition, the absence of radial compliance of the Dacron root prosthesis does not allow for an increase in diameter at the sinotubular junction STJ during ejection, which is an important aspect in providing optimal blood transport while preserving valve dynamics and valve leaflet durability. As such, the normal valve physiology is compromised in this valve-sparing intervention.

The second type of valve sparing operation, known as remodelling (FIG. 26B), involves scalloping the Dacron root prosthesis to essentially match the remaining native tissue, and using a running suture to attach the prosthesis to the native aortic root tissue. Although this method addresses some of the problems of the reimplantation method, it does not directly constrain the valve annulus diameter, which has been seen to result in annular dilatation over time. As such, this procedure is not well suited for resizing a dilated valve annulus, and may be limited to replacing aneurysmal aortic tissue. Since it also relies on a Dacron vascular conduit, which is radially non-expansible, the expansion of the aortic root at level of commissures, in the plane joining the commissures or scalloped peaks of native tissue, tends to be constrained by the conduit fabric hoop. As such, the leaflet free edges are hindered in assuming their triangulated relationship, since the plane containing the STJ is generally not expansible in this surgical procedure. Unlike the reimplantation procedure, however, the leaflets have a lower likelihood of hitting the conduit wall since pseudo-sinuses may be fashioned from a scalloped Dacron conduit to recreate the pouch-like configuration seen in a healthy aortic root. Nonetheless, in the remodelling valve-sparing intervention, the normal native valve physiology is compromised, and the effectiveness of resizing a dilated aortic annulus, or preventing its future dilatation, with a scalloped vascular conduit remains questionable.

Although useful and widely accepted for some aortic reconstruction procedures, conventional valve-sparing procedures and devices nevertheless suffer from numerous drawbacks or shortcomings that are manifested and become apparent both during the operative and post-operative periods.

Accordingly, there exists a need for an improved aortic root reconstruction procedure, and enabling devices, that allows correction of a dilated aortic annulus, or replacement of aneurysmal aortic tissue, while preserving the native leaflets and maintaining normal valve physiology. Typical prior art devices and methods for aortic reconstruction or valve sparing interventions do not offer a dynamic device configuration that may advantageously vary during the different phases of the cardiac cycle, and consequently restore or preserve normal aortic valve physiology. More specifically, there exists a need for such an aortic reconstruction device which, when implanted, dynamically controls the valve annulus both at the level of the aortic root base, and at the level of the valve commissures, thereby leading to optimal blood flow conditions therethrough and leaflet durability. Also beneficial would be a procedure with reduced time and difficulty relative to current valve sparing procedures.

SUMMARY OF THE INVENTION

It is a general object of the present invention to provide such an improved device and associated surgical method for aortic valve-sparing procedures, or other aortic root reconstruction surgeries.

Advantages of the present invention include that the proposed annuloplasty ring, by virtue of its scalloped shape, allows fixation of said ring in general proximity to the fibrous annulus of the native valve, and as such advantageously offers a dynamic ring design able to deflect a predetermined desired amount to modulate or control key dimensions of the aortic root, during the different phases of the cardiac cycle. As such, the proposed ring tends to preserve or restore normal aortic root and valve leaflet physiology during aortic valve-sparing surgeries, or aortic reconstruction surgeries. The ring is externally placed around the aortic root, thereby tending to simplify the surgical procedure.

The ring is provided with an annulus-restraining means or annulus-limiting structure or tether allowing the ring to move radially inward during muscle contractions, yet limiting or controlling the maximum diameter or dimension of the ring during phases of the cardiac cycle when the aortic root expands, in order to allow effective resizing of a dilated aortic root or valve annulus.

BRIEF DESCRIPTION OF THE DRAWINGS

Various embodiments of the present invention will now be disclosed, by way of example, in reference to the following drawings in which:

FIG. 1A, in a side elevational view, illustrates a prosthetic ring in accordance with an embodiment of the present invention.

FIG. 1B, in a top view, illustrates the prosthetic ring shown in FIG. 1A in a first ring configuration, the prosthetic ring assuming this first configuration at a time interval during a diastolic phase of a cardiac cycle.

FIG. 1C, in a top view, illustrates the prosthetic ring shown in FIG. 1A in a second ring configuration, the prosthetic ring assuming this second configuration at a time interval during a systolic phase of a cardiac cycle.

FIG. 2A, in a side elevational cross-sectional view, illustrates an aortic root with its associated anatomic structures onto which the prosthetic ring of FIG. 1A will be implanted in accordance with the principles of the present invention.

FIG. 2B, in a top view, illustrates the aortic root shown in FIG. 2A at a time interval during a diastolic phase of a cardiac cycle, with the leaflet or cusps of the aortic valve in a coapted closed leaflet configuration.

FIG. 2C, in a top view, illustrates the aortic root shown in FIG. 2A at a time interval during a systolic phase of a cardiac cycle, with the leaflet or cusps of the aortic valve in a triangulated open leaflet configuration.

FIGS. 8A-8C, in a perspective view, illustrate alternative embodiments of end fittings of a prosthetic ring according to the present invention.

FIGS. 9A-9E, in an elevational front view, illustrate alternative embodiments for an end fitting arrangement that connects two adjacent posts of a prosthetic ring according to the present invention.

FIGS. 10A-10C, in a perspective view, illustrate alternative embodiments for the terminal end of a prosthetic ring post according to the present invention.

FIGS. 11A-11C, in a sectional view, illustrate alternative embodiments for the mechanical connection between prosthetic ring post and end fitting of a prosthetic ring according to the present invention.

FIG. 12A-12C, in an elevational view, illustrate alternative embodiments for an annulus-restraining means or annulus-limiting structure of a prosthetic ring according to the present invention.

FIG. 13A-13C, in an elevational view, illustrate alternative embodiments for an annulus-restraining means or annulus-limiting structure of a prosthetic ring according to the present invention.

FIG. 14A, in a perspective view, illustrates a second embodiment for a prosthetic ring according to the present invention.

FIGS. 14B-14C, in a partial cross-sectional view, illustrate the spatial relationship between the prosthetic ring shown in FIG. 14A and an annulus-restraining hoop thereof.

FIGS. 15A-15B, in a partial elevational view, illustrate a third embodiment for a prosthetic ring according to the present invention, the prosthetic ring having a hook-in-link annulus-restraining means.

FIGS. 16A-16C, in a schematic view, illustrate an alternative embodiment for a hook-in-link annulus-restraining means of a prosthetic ring, the annulus-restraining means applying a progressively changing restraining force as a function of the prosthetic ring deflection.

FIG. 17, in a partial elevational view, illustrates a fourth embodiment for a prosthetic ring according to the present invention, the prosthetic ring having an annulus-restraining means including a shackle member.

FIGS. 18A-18B, in a partial elevational view, illustrate a fifth embodiment for a prosthetic ring according to the present invention, the prosthetic ring having an annulus-restraining means configured as a web between two adjacent U-shaped frame members of the prosthetic ring.

FIGS. 19A-19B, in a perspective elevational view, illustrate respectively a prosthetic ring having a strap-like tether and a webbed tether according to the present invention.

FIGS. 19C-19D, in a schematic top view, illustrate the base portion of the prosthetic rings shown in FIGS. 19A and 19B, in a first ring configuration and a second ring configuration, respectively.

FIGS. 21B-21G, in a schematic diagrammatic view, illustrate the geometrical relationship between the base and top dimensions of a prosthetic ring, at discrete time intervals of the cardiac cycle graphically represented in FIG. 21A.

FIGS. 22A-22C, in perspective elevational views, illustrate a sixth embodiment for a prosthetic ring according to the present invention, the prosthetic ring incorporating a vascular conduit portion.

FIGS. 23A-23C, in perspective elevational views, illustrate a seventh embodiment for a prosthetic ring according to the present invention, the prosthetic ring being designed for implantation through an endoscopic procedure, avoiding the need to incise the aorta for placement thereof.

FIGS. 24A-24D, in a schematic cutaway view, illustrate variants for suturing the prosthetic ring according to the present invention to a scalloped aortic root portion similar to the one shown in FIG. 3A.

DETAILED DESCRIPTION

Figure 3B:
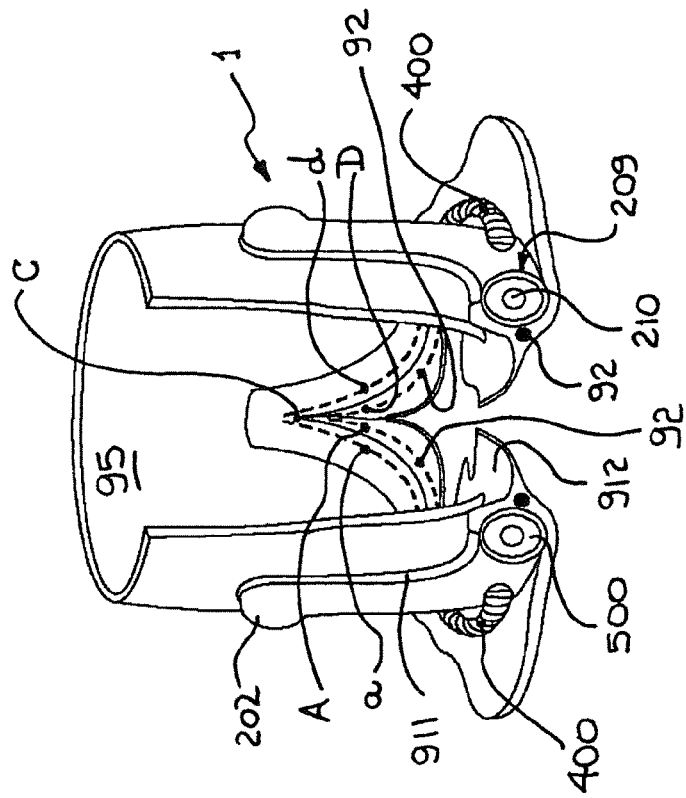
FIG. 3B, in a schematic perspective cutaway rear view, illustrates a prosthetic ring according to the present invention having been surgically implanted onto the scalloped aortic root illustrated in FIG. 3A.

Although the devices according to the present invention are disclosed herein as being used in the context of an aortic valve repair or reconstruction, the devices may also be used in any other contexts including surgical procedures of other semi-lunar valves, such as the pulmonary valve, or in the repair of other valve-containing conduits, without departing from the scope of the invention.

Referring to FIGS. 1A-1C, there is shown an aortic annuloplasty prosthesis or prosthetic ring 1 according to an embodiment of the present invention. The prosthetic ring 1 is non-planar and extends in height between a base plane (labelled BASE) and a top plane (labelled TOP). The prosthetic ring 1 resembles a crown-like structure having three circumferentially spaced apart undulations or scallops. Three generally concave, U-shaped trough sections 201 emanate from the base 206 of the ring 1 and extend axially away from said base, terminating in three spaced apart crowns or crest sections 202 at the top 207 of ring 1. As such, three alternating sinus-zones or cusp-zones 203 are delimited. Each cusp-zone 203 is generally located within one of said three trough sections 201, and extends below plane TOP. As well, three infra-commissure, inter-leaflet triangles or zones 204 are also delimited. Each inter-leaflet zone 204 is located generally below one of said three crest sections 202 and generally above plane BASE. Each inter-leaflet zone 204 generally extends between two adjacent trough sections 201.

In proximity to the plane BASE, is provided an annulus-restraining, annulus-limiting means or structure in the nature of three spaced-apart brace members 400. Each of said brace members spans to connect each of two adjacent trough sections 201. Said brace members 400 and inferior or base portions 208 of said trough sections 201 together forming a continuous perimeter 205 (FIG. 19C) in proximity to the base 206 of ring 1. As will be described in greater detail below, said perimeter 205 provides a radially compliant or conformant structure at the base 206 of ring 1 during the different phases of the cardiac cycle, but also by virtue of said brace members restrains or limits the maximum diameter that the aortic root can assume during the cardiac cycle. As such, surgical correction of a dilated aortic root, or aneurysmal aortic tissue, may be achieved through implantation of said prosthetic ring 1 according to the principles of the present invention.

With reference to FIGS. 2A-2C, the shape or profile of prosthetic ring 1 approximates the non-planar, scalloped line of collagenous, fibrous tissue forming the native annulus 92 of aortic valve 94. During the surgical intervention, ring 1 is affixed to the exterior of the aorta and aortic root 90, in close proximity and in register with the native valve annulus 92. Preferably, ring 1 is affixed in line with, or slightly below, the native valve annulus 92 using conventional techniques such as sutures. For instance, after surgical implantation, points "b" located at the base 206 of ring 1 (and located generally within plane BASE) will be in close proximity to, or in register with, points "B" designating the portion of native valve annulus 92 at the base 97 of the aortic root 90, located below the nadir of the valve leaflet 912 and in close proximity to the left ventricular outflow tract (labelled LVOT). Similarly, after surgical implantation, points "c" located on crest sections 202 of ring 1 (and located generally within plane TOP), will be in close proximity to, or in register with, points "C" designating the portion of the native valve annulus 92 at the level of the leaflet commissure 96; points "a" and "d" lying on the U-shaped trough sections 201 of ring 1, will be in close proximity to, or in register with, points "A" and "D", respectively, designating the portion of the native valve annulus 92 located substantially at mid height between the commissures 96 and base 97 of aortic root 90. As such, because ring 1 is affixed or sutured in close proximity to fibrous valve annulus 92, ring 1 can advantageously serve to resize aortic root 90, and valve annulus 92 contained therein, thereby allowing surgical correction of annulo-ectasia, aneurysm in the aortic root, or other like dilatations occurring in the native aortic tissue. As well, the attachment of ring 1 in generally close proximity to valve annulus 92 allows ring 1 to suitably regulate the geometry of aortic root 90, and spatial relationship of valve leaflets 912 during the different phases of the cardiac cycle, thereby tending to preserve or restore normal valve physiology through valve-sparing surgical procedures.

Figure 3A:
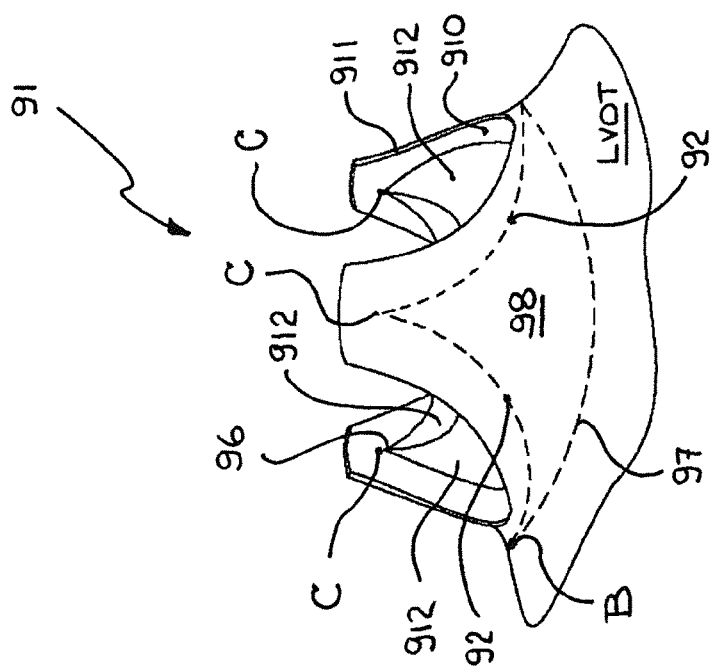
FIG. 3A, in a schematic perspective front view, illustrates an aortic root having been resected to remove the portion of aortic root tissue above the valve leaflets, the remaining scalloped aortic root readied for receiving prosthetic ring according to the principles of the present invention.

Referring now to FIG. 3A, is illustrated a scalloped aortic root 91 having been readied for valve-sparing surgical intervention by surgical resection of the aortic tissue that forms the sinuses of Valsalva, prior to implantation of ring 1. Typically, in resecting the aortic root 90, a margin or fringe 910 of aortic root tissue will be maintained, said fringe extending generally above the valve leaflets 912 and forming a scalloped free edge 911 of aortic root tissue.

As schematically illustrated in FIG. 3B, ring 1 is placed on the exterior of scalloped aortic root 91. As illustrated, in a sectioning plane in proximity to the leaflet nadir, the sectioned portion 209 of ring 1 lies adjacent to the fibrous native annulus 92, at the base 97 of the aortic root 91 and slightly above LVOT. On the posterior, non-sectioned portion of aortic root as illustrated in FIG. 3B, U-shaped section 201 of ring 1 will lie adjacent fibrous annulus 92 (shown as a dashed line), as said fibrous annulus rises above the base 97 of aortic root 91 to point "C".

An externally placed annuloplasty ring, such as ring 1 according to the present invention, tends to facilitate or simplify the surgical valve-sparing procedure. Since ring 1 is external, a less-precise ring shape that only has to approximate the valve annulus 92 may be implanted, since the potential for leaflet-to-ring interference is eliminated with an externally implanted ring. Conversely, an internally placed annuloplasty ring, as is the case with mitral and tricuspid valve annuloplasty rings, must very closely follow the native aortic annulus (and leaflet attachment perimeter) in order to avoid leaflet-to-ring interference or other such contact that may compromise leaflet physiology, leaflet coaptation, or effective blood flow therethrough. Given the complex, non-planar geometry of the aortic valve and considering the anatomic variation between patients, fashioning such an internal aortic annuloplasty ring may prove impractical and fastidious to surgically implant.

Moreover, an externally placed annuloplasty ring according to the present invention provides other advantages. By abutingly contacting the exterior surfaces of aortic root 90, ring 1 provides a bearing surface acting as a restraint or buttress capable of resizing a dilated aortic root annulus by exerting a constraining load on the dilated portion of native tissue. As such, the load imposed by the native tissue on ring-securing sutures (or alternatively other means of ring fixation) tends to be minimized hence also reducing the criticality of said sutures (or other fixation means) in securely maintaining the resized aortic root annulus. Conversely, in an internally placed annuloplasty ring, the sutures are exposed to greater tensile stresses as the dilated native tissue is urged to conform to the smaller annuloplasty ring solely by said sutures. Furthermore, since the resizing load is transmitted through the sutures, the native tissue is exposed to larger concentrated pressures at the relatively small suture interface. This may lead to tissue trauma or suture tear-through. In comparison, in externally placed annuloplasty rings, the ring structure provides a relatively larger and evenly distributed contact or bearing surface to the dilated native tissue. This tends to reduce concentrated contact stresses exerted on the dilated or oversized native tissue, and reduces the likelihood of inducing tissue trauma or suture pullout.

FIG. 3B also schematically illustrates a tubular vascular conduit 95 associated with an aortic valve-sparing procedure. Conduit 95 serves to replace the aneurysmal aortic tissue having been resected above the valve annulus 92 thereby recreating: (a) pseudo-sinuses of Valsalva, (b) the aortic conduit at the level of STJ, and (c) to the extent necessary, the portion of ascending aorta having been resected at the start of the surgical intervention. Variants of conduit 95, and more specifically the design features and construction of said variants to allow advantageous cooperation with ring 1 according to the principles of the present invention, will be described in greater detail below and in reference to FIGS. 22A-22C. Alternatively, in the case of aortic annulo-ectasia with healthy aortic root tissue, the aorta may be incised, ring 1 may then be implanted over the aortic root 90 to resize the dilated valve annulus 92 without resecting the aortic root, and the incised ends of the aorta reattached to one another, without the need for a vascular conduit.

Figure 4:
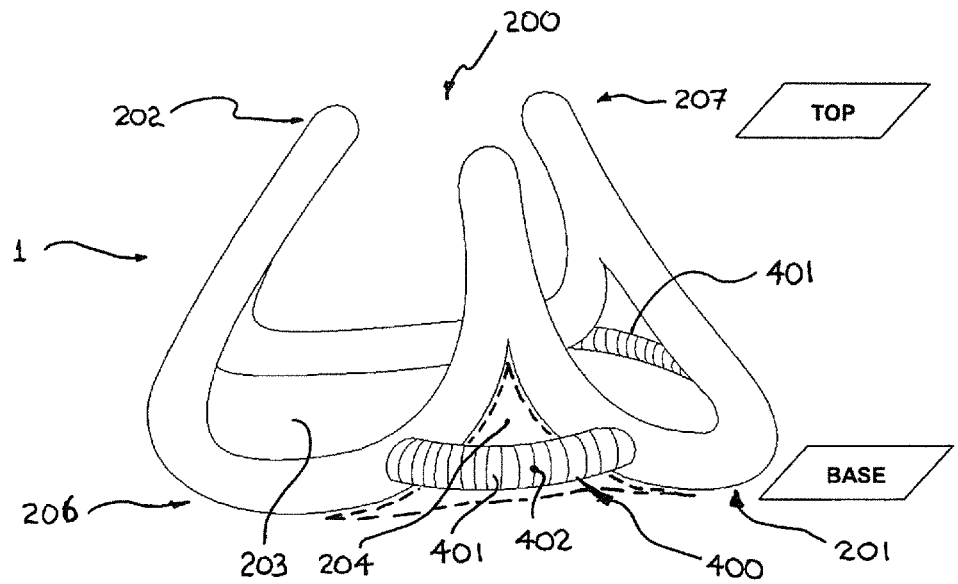
FIG. 4, in a perspective view, illustrates a first embodiment of a prosthetic ring according to the present invention.
Figure 5:
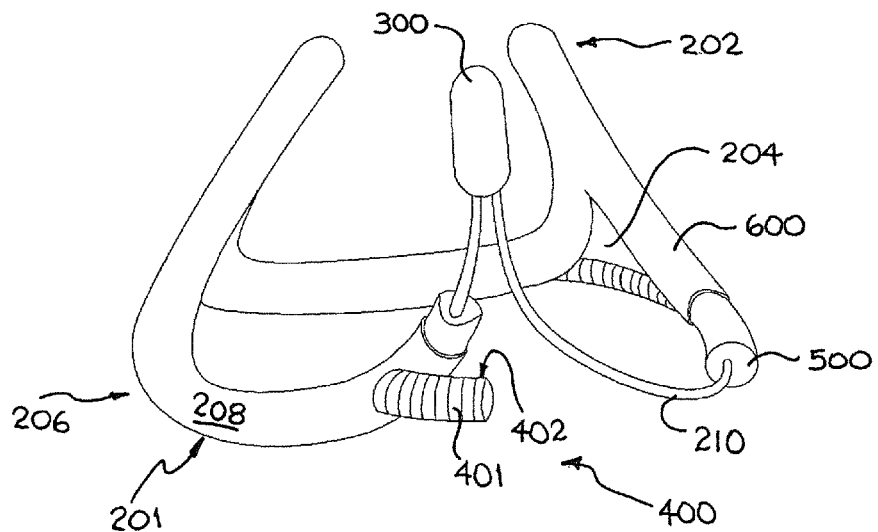
FIG. 5, in a perspective cutaway view, illustrates internal components of the prosthetic ring shown in FIG. 4.
Figure 6:
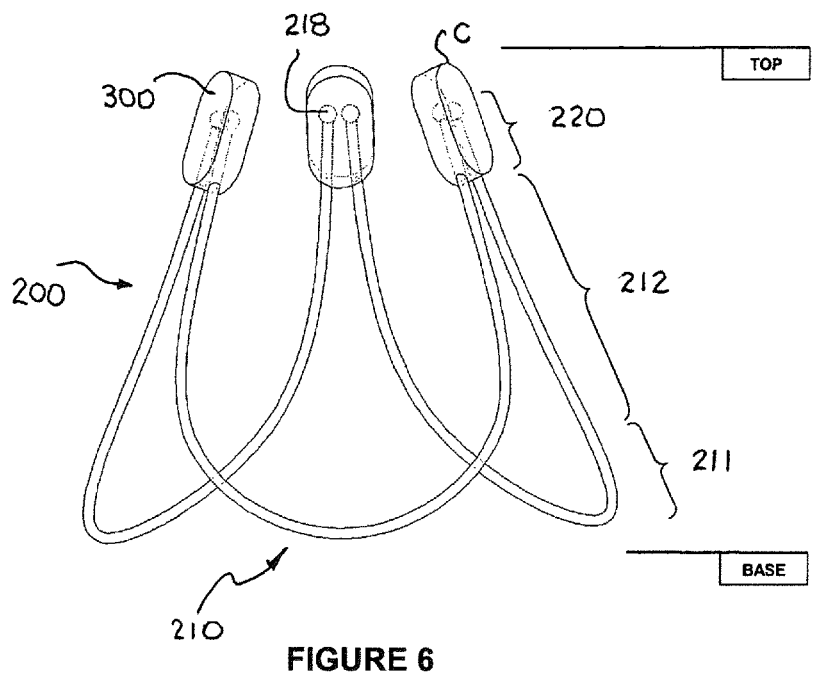
FIG. 6, in a perspective view, illustrates an undulated or scalloped ring structure of the prosthetic ring shown in FIG. 4 in accordance with the present invention.

Referring now to FIGS. 4-6, a first embodiment of ring 1 will be described in greater detail. Ring 1 consists of an undulated or scalloped three-peak ring structure, or space frame 200 and an annulus-restraining means or annulus-limiting member 400. Frame 200 is configured to form a closed, non-planar, continuous band including three trough sections 201 located in proximity to ring plane BASE, and three crest sections 202 located in proximity to ring plane TOP. Said crest sections are circumferentially interspersed between said trough sections. Said undulated space frame 200 is preferably constructed from three substantially U-shaped frame members 210. Said three frame members 210 are connected at the three resulting crests sections 202 at top 207 of ring 1 by three crown plates, end connectors, or fittings 300, and coupled at the base 206 of ring 1 by three hoop-closing members, tethers, ties or restraints 401.

Each of U-shaped frame members 210 is defined by a concave base 211 from which extend two upstanding substantially arcuate beams, wires or posts 212. When ring 1 is in its non-implanted, stress-free state, posts 212 extend in a direction generally normal to plane BASE and in a tapering, radially-inward fashion, such that the crest sections 202 are generally in closer proximity to each other than the trough sections 201. According to the principles of the present invention, such spatial relationship between said crest and trough sections is designed to vary at different times during the cardiac cycle, as will become apparent and explained in greater detail below.

U-shaped profile of members 210 (and more generally the resulting trough section 201) is configured to approximate or resemble the shape of the native valve annulus 92 over one leaflet 912, such that when implanted, said U-shaped members 210 will rest in proximity to, and generally in register with, valve annulus 912 to facilitate fixation of ring 1 thereto, preferably by sutures placed through ring 1 and valve annulus 92. Variations in patient anatomy may affect the degree of proximity or alignment between said U-shaped members and said annulus after implantation of ring 1.

U-shaped frame member 210 is preferably constructed from a biocompatible relatively-flexible material such as titanium alloy, which can elastically withstand stresses when ring 1 is exposed to variable loading during the cardiac cycle. Moreover, given a relatively flexible material, members 210 may be configured and sized with the required structural integrity to allow predetermined deflection under such cardiac loads, in a manner that achieves the desired modulation of aortic root dimensions. Additionally, the material selected for frame member 210 must be capable of withstanding the desired number of fatigue cycles in order to provide failsafe performance of ring 1 for a desired implant life.

As illustrated in a first embodiment of the present invention (FIG. 6), the U-shaped frame member 210 is preferably constructed from titanium-alloy wire having a diameter between 0.010" to "0.060", preferably between 0.020" and 0.040", and more preferably between 0.025" and 0.035". The cross-sectional profile of the wire and wire cross-sectional area may be varied along the length of wire in order to change or fine-tune the dynamic behaviour of ring 1 under load, or to optimize stress concentrations. Other metallic materials are also possible, such as stainless steels, cobalt alloys, Nitinol or other shape memory alloys. Depending on the material selected, the wire cross-sections and profiles may fall outside the preferable diameter range listed above in order to account for their different material properties relative to titanium alloy. Polymeric materials, either isotropic in nature or composite in construction, are also possible provided their design offers the desired structural integrity and fatigue life under the deflections required for adjustment or modulation of aortic root geometry.

Figures 7A, 7B, 7C, 7D, 7E:
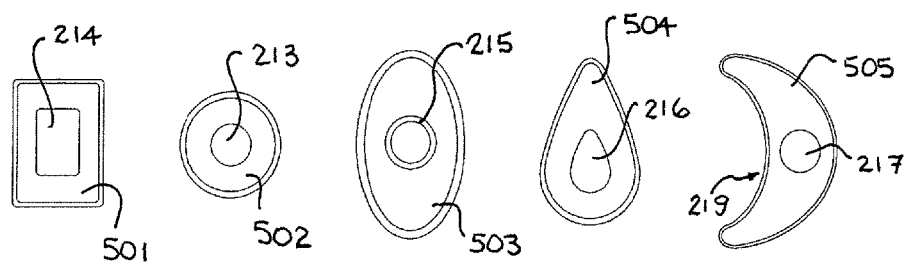
FIGS. 7A-7E, in a cross-sectional view, illustrate alternative embodiments of frame member and elastomeric sheath geometries of a prosthetic ring according to the present invention.

As illustrated in FIG. 7B, U-shaped frame members 210 are configured from wire having a circular cross-section 213, tending to facilitate the construction of ring 1. Said frame members may also be configured from strip stock 214 resulting in a frame member having a generally rectangular cross-section (FIG. 7A), or from tube stock 215 resulting in a frame member with annular cross-section (FIG. 7C), or from bar stock which may be machined, forged, or formed, or from a casting or plastic injection process to produce a frame member with a unique cross-sectional shape such as substantially cam-shaped cross-section 216 (FIG. 7D).

U-shaped frame member 210, and more specifically struts or posts 212 thereof, have terminal ends 220 that are preferably enlarged or bulbous to obtain the desired mechanical joint with end fitting 300, and desired range of relative movement between adjacent posts 212. Some or all of said terminal ends can be selectively configured such that certain types of movement of the frame member 210 relative to end fitting 300, or with respect to adjoining frame member 210, can be either constrained or free. As illustrated in FIG. 6, terminal ends are substantially spherical or ball shaped 218. As such, spherical ball ends 218 allow ball-in-socket type of movement or articulation of post 212 relative to said fitting 300, insofar as a gap is provided therebetween to allow such articulation. Spherical end 218 does however axially retain post 212 relative to end fitting 300. Alternatively, as illustrated in FIG. 10A, terminal end 220 may be configured with an enlarged cylindrical protrusion 221 that is generally aligned with longitudinal axis of post 212. As such, the mechanical joint between cylindrical terminal end 221 and cylindrical volume within fitting 300 allows rotation 223 of post 212 about its long axis, while axially retaining post 212 within fitting 300. Both embodiments illustrated in FIGS. 6 and 10A may advantageously serve to reduce stresses in U-shaped frame member 210 during deflections of ring 1 occurring at different phases of the cardiac cycle. A further embodiment of a terminal end 220 consists of bending the terminal end of a circular cross-section post 212. When such bent terminal end 224 is coupled with an appropriate end fitting 300, the resulting mechanical joint will permit rotation 226 of said post about a rotation axis 225 aligned with the centreline of bent terminal end. For example, the rotation axis 225 may be either tangent to the diameter defined by three crest sections 202 lying in plane TOP, or normal to said diameter, or even assume an orientation between normal and tangent to said diameter. The bent terminal end 224 also serves to retain post 212 within end fitting 300. Yet another embodiment for a configuration of terminal end 220, as illustrated in FIG. 10C, consists in having a cube-shaped terminal end 227, or enlarged terminal end with at least two opposed flats. Such a terminal end would essentially restrict all relative movement between post 212 and fitting 300, provided said fitting is configured with an appropriate mating depression or groove to receive said cube-shaped terminal end 227. Other variants for a terminal end are also possible without departing from this aspect of the invention.

Referring now to FIGS. 5 and 6, ring 1 is configured with three end fittings 300 providing a mechanical connection between adjacent U-shaped frame members 210, and more specifically terminal ends 218 of post 212 thereof. Said end fittings offer many advantages. One such advantage is that, by preventing direct contact between frame terminal end 220 and native aortic tissue, end fittings 300 act as bearing plates or surfaces tending to reduce and uniformly distribute ring contact stresses around the commissures 96. Another advantage provided by fittings 300 consists in reducing the maximum or peak bending stresses that frame member 210 will experience under deflection of ring 1, by allowing relative movement between end fitting 300 and frame terminal end 220. Yet another advantage provided by end fittings 300 consists in facilitating the fabrication of a scalloped or undulated ring structure 200 by providing mechanical connection of smaller, easier to fabricate components such as frame member 210.

End fitting or crown plate 300 may be fabricated from a variety of metallic or polymeric materials, depending on the type of mechanical joint desired. In the first embodiment illustrated in FIG. 6, fitting 300 is made from medical grade polymer suitable for plastic injection molding, such as polypropylene or PEEK, which can be over-molded to terminal ends 220 of posts 212. As previously discussed, terminal ends 220 are preferably configured with one of a variety of terminal end geometries in order to achieve the desired mechanical joint between end fittings 300 and frame member 210. Alternatively, terminal ends 220 of adjacent frame members 210 may be: (i) welded together at a weld location 230 and crimped to metallic plate 231 at crimp locations 232 (FIG. 9A); (ii) crimped to metallic plate 233 at crimp location 234 (FIG. 9B); (iii) welded simultaneously to one another and to metallic sub-plate 235 to form a weld bead 236 (FIG. 9C); or (iv) glued to a metallic or plastic sub-plate 237 at glue location 238 (FIG. 9D).

Although less advantageous, as illustrated in FIG. 9E, terminal ends 220 of two adjacent U-shaped frame members 210 may alternatively be joined together by a weldment or brazed joint 239 (if metallic), or glued together in a glued joint 240 (if polymeric). As such, the advantages associated with having a crown plate 300, as previously recited above, would not be exploited in such a ring structure. Alternatively still, the three U-shaped frame members 210 may be produced in a single, unitary piece thereby also eliminating said weld or glue joint 239, 240.

According to a first embodiment, ring 1 is preferably configured and sized such that when said ring is implanted, crown plates 300 are preferably in register with, or in close proximity to, commissures 96. Variants of ring 1 may also be designed such that, in use, crown plates 300 extend above commissures 96 and fibrous annulus 92, for example extending till or slightly above the level of the STJ, or alternatively below said commissure and annulus within inter-leaflet zone 204. As will be discussed in greater detail below, the spatial relationship between said crown plates and said commissures may have an effect on method of suturing.

FIGS. 8A-8C illustrate variants to the geometry, configuration or size of end fitting 300 that aim to optimize stress distribution and transfer of loads between post 212 and end fitting 300. Said stresses and loads are exerted on fittings 300 by U-shaped frame members 210, when said frame members are exposed to and react cardiac loads from a dynamic aortic root 90. For example, one variant illustrated in FIG. 8A, involves extending the mechanical interface between end plate 310 and posts 250 to cover a greater length 311 of said post, in a gradually tapering manner towards base 206 of ring 1. This provides a larger mechanical interface or transition zone rather than simply covering, encapsulating, or enclosing the terminal-most length 220 of said post in a manner as illustrated in previously described FIG. 6. As such, the variant in FIG. 8A would distribute the stresses generated from the deflections 314 of post 250 (said deflections in a plane 313 containing plate 310 and posts 250), over a larger contact or bearing surface 311 at plate-to-post interface 315. Similarly, the variant in FIG. 8B would distribute the stresses generated from the deflections 325 of post 251 (said deflections in a plane 324 that is substantially normal to plane 323 containing plate 320 and posts 251), over a larger contact or bearing surface 321 at plate-to-post interface 322. In another example of a variant illustrated in FIG. 8C, end plate 330 is tapered at the interpost junction 331 occurring between adjacent posts 252, 253. Such a tapering feature would allow angular deflections of one post 253 about a rotation axis 333 that is coincident with longitudinal axis of adjacent post 252. One of the key aspects of the features just described with reference to FIGS. 8A-8C, is that such features allow for wire or post stresses, that are generated by relative movement or deflections between adjacent wires or posts, to be distributed and shared with cooperating end fittings. This distribution and transfer of stresses to said cooperating end fitting tends to improve fatigue life of wire or posts when they are subjected to cyclic cardiac loading.

In controlling, modulating, or adjusting key dimensions of the aortic root 90 following implantation of ring 1, it may be advantageous to allow relatively free or unhindered motion between wire or posts 212 and end fitting 300, said relatively free motion being within a predetermined range of motion resulting from the design interface between said post and said end fitting. In one embodiment according to this aspect of the invention, as illustrated in FIG. 11A, fitting 340 is configured with a clearance channel 341 extending longitudinally over a length 342 of wire or posts 259, said channel 341 having a width larger than said wire or post thickness. The width of channel being larger than the wire or post thickness results in a predetermined range of relatively free angular deflection 343 within which wire or post 259 can angularly deflect before contacting channel walls 344 (i.e., angular range of freedom). Preferably, said channel width is tapering in size as channel 341 approaches post-to-fitting encapsulation zone 345.

In another embodiment according to this aspect of the invention, as illustrated in FIG. 11B, end fitting 350 is configured with two keyways 351. Each of wires or posts 254 is configured with an appropriately shaped cooperating key 255 that allows rotation of said key within said keyway due to a preset clearance therebetween. The angle of keyway sector 352 being larger than the angle of key sector 256 results in a predetermined range of relatively free angular deflection 353 within which said key can rotate within said keyway before it contacts stops 354. As such, post 254 can rotate about its longitudinal axis a predetermined amount before contacting stops 354 (i.e., torsional range of freedom).

In yet another embodiment according to this aspect of the invention, as illustrated in FIG. 11C, end fitting 360 is configured with two elongate channels or trackways 361 extending along length 362 of fitting 360 in a direction substantially aligned with height 363 of ring 1. Trackway 361 is configured and sized such that terminal ball end 257 of wire or post 258 is slidingly engaged therewithin. This allows relatively free translational movement of wire or post 258 relative to end fitting 360, within a predetermined range of translational motion, said predetermined range limited by terminal ball end 257 coming into contact with either stop 363 or trackway top 364 (i.e., linear or translational range of freedom). Such an embodiment is advantageous in providing a ring 1 with a variable height 363.

A post-to-fitting design interface as described above in reference to FIGS. 11A-11C, will also have the effect of distributing or transferring post stresses to cooperating fitting, only after a deflection therebetween exceeds said predetermined range of relatively free movement, and post, or terminal end thereof, comes into contact with motion-limiting features of said fitting. These features may be combined, or used individually, to control, modulate, or limit key dimensions of aortic root 90 during the cardiac cycle.

In another aspect of the present invention, illustrated in FIG. 19B, crown plate 300 may be advantageously provided with an aperture 370 to allow suturing of ring 1 at commissures 96. Moreover, aperture 370, also extending through crest section 202 of ring 1, may also advantageously provide a fixturing means for demountably engaging ring 1 with an annuloplasty ring holder (not shown), said holder serving to hold and manipulate ring 1 during surgical implantation thereof. Said holder may be configured and sized for engaging said apertures 370 preferably while simultaneously spreading apart crest sections 202 (relative to their non-stressed, free state configuration) thereby tending to facilitate implantation of ring 1. Alternatively, aperture 370 may be replaced by a blind hole or any other suitable mechanical interface capable of providing demountable engagement with an annuloplasty ring holder.

In a first embodiment of the present invention (FIG. 5), structure or frame 200 is preferably covered by a substantially elastomeric covering, layer or sheath 500. Elastomeric layer 500 is preferably manufactured from a biocompatible material such as silicone rubber, polyurethane, synthetic or natural rubber approved for implant use, elastic hydrogels, polyvinyl alcohol, or other like substantially elastic biocompatible materials that do not considerably rigidify the structure of underlying U-shaped frame member 210. In a first embodiment of the present invention, elastomeric layer 500 is enveloped or covered by an outer textile or fabric covering 600.

Elastomeric layer 500 provides a variety of functions and advantages. One function of said elastomeric layer is to provide an improved or increased contact area between ring 1 and aortic root 90. As well, due to its elastomeric material properties, said layer provides a relatively softer, less traumatic, cushioned contact surface with aortic root tissue than the stiffer, metallic U-shaped frame member 210. Another function of elastomeric layer 500 is to provide volume between the relatively thin frame member 210 and fabric covering 600, so as to limit or prevent unwanted tissue ingrowth that may otherwise occur in the resulting space or residual volume between member 210 and covering 600 in the absence of elastomeric layer 500. A further advantage offered by said elastomeric layer is to enhance suture pullout strength of ring 1, while reducing loading on fabric covering 600, when ring fixation sutures are placed through said elastomeric layer. In a further advantage still, elastomeric layer 500 may be used as a biocompatible covering to shield an underlying core material that may exhibit inferior biocompatibility. For instance, the elastomeric layer may cover the end fittings 300 of ring 1 if said fittings exhibit inferior biocompatibility. The elastomeric layer 500 may also be advantageously used to cover all constituent parts of a composite ring structure, thereby providing a containment envelope or encasement capable of trapping said constituent parts in the event of a ring failure or rupture between said constituent parts. Finally, elastomeric layer 500 may be applied strategically to U-shaped frame member 210, either at select locations or in varying thicknesses, so as to tune the dynamic response of scalloped ring structure 200.

With reference to FIG. 5, elastomeric layer 500 preferably covers the U-shaped wire frame 210 and end fittings 300. Elastomeric layer or sheath 500 may be applied to underlying structure and more specifically U-shaped frame member 210 in a variety of thicknesses and cross-sectional shapes in order to best exploit one or several of the advantages described above. For example, elastomeric layer 500 may be applied with a uniform thickness around the underlying frame member 210, resulting in a cross-sectional shape of elastomeric layer 500 being similar to that of said frame member except for being equally offset therefrom by the sheath thickness. For example, FIG. 7A illustrates an embodiment having an elastomeric layer 501 with substantially rectangular outer profile achieved by having an equal thickness elastomeric sheath around a substantially rectangular core 214; FIG. 7B illustrates an embodiment having an elastomeric layer 502 with substantially circular outer profile achieved by having an equal thickness elastomeric sheath around a substantially circular core 213; FIG. 7D illustrates an embodiment having an elastomeric layer 504 with substantially tear-drop outer profile achieved by having an equal thickness elastomeric sheath around a substantially cam-shaped core 216.

Alternatively, said elastomeric sheath thickness may be of variable thickness around said core or underlying frame structure resulting in a sheath cross-sectional shape that is unevenly offset, or completely unrelated to the frame cross-sectional shape. For example, FIG. 7C illustrates an embodiment having an elastomeric layer 503 with substantially elliptical outer profile achieved by having an unequal thickness elastomeric sheath around a substantially tubular core 215; FIG. 7E illustrates an embodiment having an elastomeric layer 505 with substantially crescent-shaped outer profile achieved by having an unequal thickness elastomeric sheath around a substantially circular core 217.

The embodiments illustrated in FIGS. 7C and 7E, in addition to providing an increased bearing surface of the ring structure 200 against the aortic wall, or aortic root conduit, have the additional benefit of providing a larger area through which to apply ring fixation sutures. Furthermore, the embodiment of FIG. 7E provides the additional benefit of closely conforming to the native anatomy of the aortic root 90 by having a generally concave tissue-contact surface 219.

With reference to FIG. 5, an outer textile layer or fabric covering 600 preferably covers elastomeric layer 500. Textile layer 600 is preferably made from materials including, but not limited to, polyester, polypropylene, polytetrafluoroethylene (PTFE), microporous expanded polytetraflouroethylene (ePTFE), polyethylene terephthalate (Dacron), polyamide (Nylon), polyethylenterephthalate (PET), or other like fabrics appropriate for implant use. Said textile layer may also be advantageously treated with bioactive agents or surface treatments to limit foreign body response and promote favourable tissue ingrowth after implantation of ring 1. Preferably, said textile layer or fabric covering is between 0.005" and 0.020" in thickness. One function of fabric covering 600 is to provide a means for suturing the implantable ring 1 to native anatomic tissue, or to an aortic root prosthesis that may be used in conjunction with ring 1. Another purpose of said fabric covering is to provide a suitable surface for the post-implantation growth of cells and tissue, helping to mitigate long-term foreign-body response and reduce the likelihood of infection and other complications.

With reference to a first embodiment of the present invention, and to FIGS. 1A through 5, the annulus-restraining means or annulus-limiting structure 400 and the function it provides will now be discussed in greater detail.

The main function of annulus-restraining means 400 is to limit the maximum diameter or dimension at the base 206 of ring 1, while allowing substantially unhindered radially inward deflections at ring base 206. Deflections at ring top 207, both radially inward and outward, are preferably substantially unhindered by said means 400. As such, since ring 1 is secured during surgery to aortic root 90, and more specifically valve annulus 92 thereof, ring 1 also adjusts the dimensions of aortic root 90, controls the variations of said dimensions, or limits deformations thereof, said adjustment or control governed at least in part by said means 400.

Annulus-restraining means 400 extends from one U-shaped trough section 201 to an adjacent U-shaped trough section 201, spanning across interleaflet zone 204 therebetween (FIG. 1A-1C). Preferably, as illustrated, each of three interleaflet zones 204 (delimited by dashed line perimeter in FIG. 4) is spanned by an annulus-restraining means or structure 400. Alternatively, variants of ring 1 may also be configured having annulus-restraining means or structure 400 that only spans across one, or two, of the three said interleaflet zones 204.

In FIG. 4, in a preferred first embodiment of ring 1, is illustrated an annulus-limiting structure or annulus-restraining means 400 in the nature of a hoop-closing member, tie, restraint, strap or tether 401.

Tether 401 may be constructed from a textile or fabric structure that is configured with a plurality of pleats 402 to allow controlled expansion or limited deformation of ring 1, and more specifically base 206 thereof, in a direction generally perpendicular to the axis defining the fold of said pleats. Fabric tether 401 may be either an integral component woven or knit directly into the fabric covering 600 of ring 1, or may be independently woven, knit, or produced and subsequently assembled to ring 1 as an additional part or component. By configuring said tether 401 with an appropriate number, geometry and depth of pleat 402, ring 1 can be made to be expansible up to a limit point when said pleats are substantially flattened or unfolded, at which point ring 1, and aortic root 91 attached thereto, would be limited, restrained or modulated from further expansion.

During contraction of the heart muscle near the outflow tract LVOT, and more specifically during annulus-reducing contraction of aortic root base 97, pleats 402 resume their folded or pleated configuration. As such, pleats 402 impose little or no restraint on ring 1 as it deflects radially inward during said contractions, thereby allowing the ring 1 to contract at base 206 and assume a smaller diameter or size in compliance with the aortic root. This behaviour of ring 1 generally reflects the normal physiology of the aortic root 90, whose dimension or geometry is dynamic, and varies as a function of ventricular muscle relaxation or contraction and blood pressures within said aortic root. Folding action of pleats 402 would allow ring base 206 to decrease in diameter, or dimension, up to its predetermined minimum, and substantially without interference to surrounding body tissues. Pleating, as such, eliminates the formation of larger folds in textile or fabric structures, or other like structures, when ring 1 deforms. Formation of larger folds may negatively affect tissue ingrowth into portions of implanted ring 1, or may insult surrounding tissue as said larger folds accommodate said contraction of ring base 206.

Tether 401 is designed to act primarily when it is exposed to a tensile load, such tensile load occurring typically when aortic root 90 wants to expand during the variable cardiac cycle. Tether 401 is designed to have little or substantially no effect on radially inward deflections of aortic root tissue, especially in said deflections occurring within interleaflet triangle 98 of said aortic root (FIG. 3A).

As such, the base diameter 97 of aortic root 91 (and of valve annulus 92) may be regulated or controlled by tether 401 which allows substantially unhindered radially inward deflections of aortic root tissue, but limits the maximum base diameter 97 with the aim of resizing the dilated native aortic root 90, restoring leaflet 912 coaptation, and correcting aortic insufficiency or regurgitation. During said radially inward deflections of aortic root tissue, trough sections 201 move closer together as tether 401 allows native aortic tissue, especially in interleaflet triangle 98, to contract or deflect inwardly. During radially outward deflections of aortic root tissue, ring base 206 also deflects radially outward and trough sections 201 move apart relative to each other, until the effect of tether 401 sets in and starts to limit and eventually restrain any such further radially outward deflections.

Tether 401 advantageously provides the ability for a scalloped ring structure 200 to resize a dilated aortic root 90 (and dilated valve annulus 92 therein), while also preserving the flexibility and radial compliance of said scalloped ring structure. In contrast, attempting to resize a dilated aortic root with a flexible scalloped ring structure not benefiting from the effect of tether 401 would result in flattening of ring scallops or undulations. Flattening of ring scallops would result in a corresponding increase in diameter of ring base as said scalloped ring is exposed to loads from an expanding pressurized aortic root. If said scalloped ring is in turn stiffened to prevent said unwanted flattening of scallops, the resulting structural stiffness may be too high to allow the desired radially inward compliance of scalloped ring at its base, or deflection of crest sections 202 at its top, during the varying cardiac cycle. As such, a stiffened scalloped ring without tether would not allow resizing of a dilated aortic root in a manner that tends to preserve the normal physiology of a dynamic native aortic root.

Preferably, as illustrated in FIG. 4, annulus-restraining means or structure 400 is located in general proximity to base 206 of ring 1. Preferably, said means or structure 400 is located between plane BASE and one-half the height between planes BASE and TOP, and more preferably in between one-eighth to one-third of said height. Without departing from the spirit of the invention, variants of ring 1 may be configured with means or structure 400 located anywhere within substantially triangular inter-leaflet zone 204, above plane BASE and below crest sections 202. Moreover, said means or structure 400 may be configured in a variety of sizes or dimensions within said inter-leaflet zone 204, ranging from a strip-like geometry (FIG. 19A) to a web-like geometry (FIG. 19B).

Referring now to FIGS. 12A-12C, are illustrated alternative embodiments of an annulus-restraining means or annulus-limiting member 400 of the ring 1. FIG. 12A illustrates an annulus-restraining means in the nature of a substantially stretchy, generally flexible rubber strap or elastomeric tether 402. Elastomeric tether 402 may be made from the same material as the elastomeric layer 500 used to cover the U-shaped frame members 210, and as such tether 402 extends therefrom as an integral extension or link. Alternatively, elastomeric tether 402 may be made from a different formulation, or material, that may be overmolded, glued, or bonded to the previously produced elastomeric sheath or layer 500, or to frame members 210, and as such defining a composite assembly for ring 1. Alternatively still, ring 1 may be configured with frame members 210 being replaced by elastomeric layer 500.

FIGS. 12B-12C illustrate an annulus-restraining means 400 in the nature of a fibre-reinforced silicone tether 403. Silicone tether 403 is draped between adjacent frame members or posts 210, said tether being in general proximity to the base of the inter-leaflet triangle 204. A fibre-reinforcement 404 contained within silicone tether 403 is designed to approximate the visco-elastic behaviour of the native aortic root tissue; that is, offering compliance or flexibility with increasing stiffness as the diameter of ring base 206 increases. FIG. 12B illustrates silicone tether 403 in a non-stretched, relatively flexible configuration. In this flexible configuration, said fibre-reinforcement 404 provides substantially little or no stiffening. FIG. 12C illustrates silicone tether 403 in a stretched, relatively stiff configuration. In this stiff configuration, fibres of said fibre-reinforcement provide stiffening that substantially prevents further elongation of said tether 403. Optionally, silicone tether 403 may also be covered with a pleated or crimped fabric (similar to 401) that allows said tether to stretch between said flexible and stiff configurations.

Referring now to FIGS. 13A-13C, are illustrated further alternative embodiments of an annulus-restraining means or annulus-limiting member 400 of the ring 1. FIG. 13A illustrates an annulus-restraining means 400 in the nature of an elastically deformable undulated tie 405. Tie 405 is preferably metallic in construction such that it can be joined or connected to span between two adjacent metallic U-shaped frame members 210. An elastic sheath 406, similar to elastomeric layer 500 used to cover U-shaped frame members 210, preferably covers tie 405. Undulations 407 in tie 405 will progressively straighten out as ring 1 expands at its base 206, thereby providing a progressively increasing annulus-restraining load with increasing ring 1 diameter. Ring 1 is limited to further radial expansion when said undulations are substantially flattened. Tie 405 is designed with the appropriate geometry and number of undulations such that, for a predetermined range of ring 1 annulus expansion (and circumferential elongation of tie 405), the material properties of said tie will not be exceeded and, as such, said tie can elastically resume its undulated configuration during variations in the cardiac cycle. FIG. 13B illustrates an annulus-restraining means 400 in the nature of an elastically deformable loop 408. FIG. 13C illustrates an annulus-restraining means 400 in the nature of an elastically deformable spring member 409.

Referring now more specifically to FIGS. 14A-14C, there is shown a prosthetic aortic annuloplasty ring 2 in accordance with a second embodiment of the present invention. Ring 2 is substantially similar to ring 1 already described, hence, similar reference numerals will be used to denote similar components. The main difference between ring 1 and 2 is in the annulus-restraining means or annulus-limiting structure, which in this second embodiment consists of a hoop-and-eyelet arrangement 410. A plurality of eyelets 411 is circumferentially disposed around the base portion 206 of ring 2, and more specifically, as illustrated, two such eyelets 411 are attached to each of three U-shaped trough sections 201. A cooperating belt or hoop member 412 is inserted through each of said eyelets, and as such said hoop member 412 is coupled to ring 2. A radial clearance 413 between trough sections 201 and hoop member 412 allows ring 2 to deflect at its base 206 without being affected by hoop member 412. Over a predetermined range established by said radial clearance 413, the base 206 of ring 2 may undergo radial deflections without being controlled or modulated by hoop member 412 (FIG. 14B). Beyond the limits of said predetermined range, ring base 206 (and more specifically trough sections 201 thereof) comes into contact with said hoop, and as such said ring base (and aortic root 90,91 attached thereto) is restrained or limited from further radially outward deflection (FIG. 14C). Hoop 412 restrains ring 2 from further outward radial movement, to the extent that hoop 412 flexibility will allow, based on its design and material properties. For example, a very stiff hoop 412 may entirely prevent further radial outward deflections of ring 2, while an elastic hoop 412 will restrain further deflections of ring 2 to the degree that its radial stiffness will permit. As such, the design of hoop 412 may be optimized to provide the desired amount of restraint to appropriately modulate the base 97 of the aortic root 91 and also limit the maximum diameter of the native valve annulus 92. Hoop 412 may be fabricated from a metallic, polymeric, or textile material. Eyelet 411 may be configured as an extension of textile covering 600, or an elastomeric eyelet configured as a part of the elastomeric layer 500, or even connected or coupled to U-shaped frame member 210. The other difference between ring 1 and 2 is that, in ring 1, the annulus restraining means in nature of tether 401 spans only across interleaflet zone 204, while in ring 2, the annulus restraining means in nature of hoop-and-eyelet arrangement 410 spans across interleaflet zone 204, and also therebeyond.

Referring now more specifically to FIGS. 15A-15B, there is shown a prosthetic aortic annuloplasty ring 3 in accordance with a third embodiment of the present invention. Ring 3 is substantially similar to ring 1, hence, similar reference numerals will be used to denote similar components. As illustrated, only the portion of ring 3 in proximity to one of the infra-commissure zones 204 is shown. The main difference with ring 1 is in the annulus-restraining means or annulus-limiting structure, which in this third embodiment consists of a hook-in-link arrangement 420. Said arrangement 420 includes three loop or link members 421, each of which is attached to a different U-shaped trough section 201 in proximity to ring base 206 of ring 3. Each of said links 421 extends circumferentially within their respective infra-commissure zone 204, from trough section 201 to which they are attached towards the adjacent trough section 201. Cooperating with said link members are three hook members 422. Each of hook members 422 is also attached to a separate U-shaped trough section 201 of ring 3, and extends from trough section 201 to which they are attached towards a cooperating link member 421 that is attached to an adjacent trough section 201. A tangential or circumferential clearance 423 between cooperating link 421 and hook 422 allows ring 3 to deflect at its ring base 206 without being affected by said hook-in-link arrangement 420. Over a predetermined range established by said circumferential clearance 423, ring base 206 may undergo radial deflections without being controlled or modulated by said hook-in-link arrangement (FIG. 15A). Beyond the limits of said predetermined range, said hook comes into contact with said link, and as such the ring base 206 (and aortic root 90,91 attached to ring 3) is restrained or limited from further radially outward deflection (FIG. 15B). Hook 422 may be fabricated from a metallic or polymeric material. Link 421 may be configured as a fabric loop extending from textile covering 600, or an elastomeric link configured as a part of elastomeric sheath 500, or even a metallic or polymeric link connected to frame member 210.

FIGS. 16A-16C schematically illustrate a variant 430 to the hook-in-link arrangement 420 of ring 3. An elastic component or spring member 431 is introduced between trough section 201 and hook 422, and adjacent trough section 201 and link 421. Similar to the embodiment illustrated in FIG. 15A, over a predetermined range established by the circumferential clearance 423, ring base 206 of ring 3 (and three trough sections 201 thereof) may undergo radial deflections without being controlled or modulated by said hook-in-link arrangement 430 (FIGS. 16A and 16B). Beyond the limits of said predetermined range, said hook 422 comes into contact 432 with said link 421, at which point the spring stiffness of spring members 431 would come into effect and progressively increase the restraining force exerted by hook-in-link arrangement 430 between two adjacent trough sections 201.

Referring now to FIG. 17, there is shown a prosthetic aortic annuloplasty ring 4 in accordance with a fourth embodiment of the present invention. Ring 4 is substantially similar to ring 1, hence, similar reference numerals will be used to denote similar components. As illustrated, only a portion of ring 4 in proximity to one of the infra-commissure zones 204 is shown. The main difference with the first embodiment is in the annulus-restraining means or annulus-limiting structure, which in this fourth embodiment consists of a shackle arrangement 440. Six pin members 441 are circumferentially disposed around the ring base 206 of ring 4. As illustrated, two of the six pins 441 are shown, one pin attached to a first trough section 201 and another pin attached to an adjacent trough section 201. A generally elongate strap member or shackle 442 is slidingly connected to two adjacent pins 441 thereby spanning the infra-commissure zone 204 therebetween and, as such, also being coupled to ring 4. Each shackle 442 is configured with at least one elongate slot or channel 443 within which at least one of said pins 441 is free to slide. As illustrated, shackle 442 is configured with a pair of channels 443, one said channel for engagement with one of pins 441. A tangential or circumferential clearance 444 between pin 441 and end of slot 443 allows ring base 206 of ring 4 (and more specifically trough section 201 thereof) to deflect substantially without being affected by said shackle 442. Over a predetermined range established by said circumferential clearance 444, ring base 206 of ring 4 may undergo radial deflections without being controlled or modulated by shackle 442. Beyond the limits of said predetermined range, pin 441 comes into contact with one of the extremities of said shackle slot 443, and as such ring base 206 (and aortic root 90 or 91 attached thereto) is restrained or limited from further radial deflections. Shackle 442 restrains ring 4 from further radial movement, to the extent that shackle flexibility will allow based on its design and material properties. For example, a very stiff shackle 442 can entirely prevent further radial outward deflections of ring base 206, while an elastic shackle will restrain further deflections of ring base 206 to the degree that its structural stiffness will permit. Shackle 442 may be fabricated from a metallic, polymeric, or textile material. Pin 441 is preferably attached to and protruding from U-shaped frame member 210. Alternatively, shackle 442 may be fixedly attached at one end to frame member 210, and slidingly attached to frame member 210 at opposed end through pin 441.

Referring to FIGS. 18A and 18B, there is shown a prosthetic aortic annuloplasty ring 5 in accordance with a fifth embodiment of the present invention. Ring 5 is substantially similar to ring 1, hence, similar reference numerals will be used to denote similar components. As illustrated, only a portion of ring 5 in proximity to one of the infra-commissure zones 204 is shown. The main difference with the first embodiment is in the annulus-restraining means or annulus-limiting structure, which in this fifth embodiment consists of a webbed tether arrangement 460. In FIG. 18A, fabric covering 600 extends below crest sections 202 (and below end fitting 300), and is draped between two adjacent U-shaped trough sections 201 to substantially cover infra-commissure region 204 with a fabric or textile web 461. Said textile web 461 is preferably made from pleated or crimped fabric. Textile web 461 may be made of the same material as fabric covering 600 and extending therefrom as an integral part thereof, or made as a separate part from either a similar or different material and assembled to ring structure 5 to form a composite assembly. Textile web 461 may be of a woven or knit construction, or other textile construction that allows or promotes the function of a tether as described above in reference to the first embodiment.

In a variant of this fifth embodiment, illustrated in FIG. 18B, ring 5 is configured with the elastomeric layer or sheath 500 extending below crest sections 202 and end fittings 300, and is draped between two adjacent U-shaped frame members 210 in a manner to substantially cover infra-commissure zone 204 with an elastomeric web 462. Elastomeric web 462 may be of variable thickness along its height, circumferential width, or both, in order to fine-tune the flexibility or elasticity of said web 462 to allow proper modulation or control of dimensions of aortic root 90 by ring 5. Elastomeric web 462 may also be made from a different material than elastomeric sheath 500. Alternatively, web 462 may be made as a composite construction having fibre reinforcement at strategic locations therein to tailor flexibility of said web in certain directions. Alternatively still, at least a portion of said elastomeric web 462 may also be covered by a textile fabric covering similar to textile fabric used to make web 461.

In reference to FIG. 19A, the three inferior or base portions 208 of trough sections 201 coupled with the three tether members 401, together form a substantially circular ring perimeter 205. Similarly in FIG. 19B, the three base portions 208 coupled with the three textile web members 461, together form a substantially circular ring perimeter 205.

Said ring perimeter 205 is schematically illustrated in FIG. 19C which shows ring 1 in a first ring configuration 280 occurring generally during diastole, and in FIG. 19D which shows ring 1 in a second ring configuration 290 occurring generally during systole. Also illustrated in FIGS. 19C and 19D, is the effect of tether 401 on ring base 206, and more specifically inferior or base portions 208 thereof. In FIG. 19C, said tether 401 permits ring base portions 208 to deflect radially inward, in a substantially free and unhindered manner, and in compliance with dynamic aortic root movement during the diastolic phase of cardiac cycle. In FIG. 19D, said tether 401 limits ring base portions 208 to deflect radially outward only a predetermined amount, said amount established by the effect of tether 401. As such, the maximum diameter at base 97 of aortic root 91 is restrained by tether 401, typically during the systolic phase of the cardiac cycle. Variations in diameter at base or aortic root are controlled or modulated by tether 401 as ring 1 changes configuration between said first 280 and second ring configurations 290.

Referring to FIG. 19A, the annulus-restraining means or annulus-limiting structure in nature of tether 401 results in a fenestrated arrangement within the inter-leaflet zone 204, with one aperture 451 created respectively between said tether 401 and below crest section 202. Alternatively, rings may be designed with a combination of one or more tethers 401 spanning over said inter-leaflet zone 204 resulting in a fenestrated arrangement with a plurality of apertures (not shown). Referring to FIG. 19B, annulus-restraining means or annulus-limiting structure in nature of web 461 results in a non-fenestrated arrangement within the inter-leaflet zone 204.

Figures 20A, 20B, 20C:
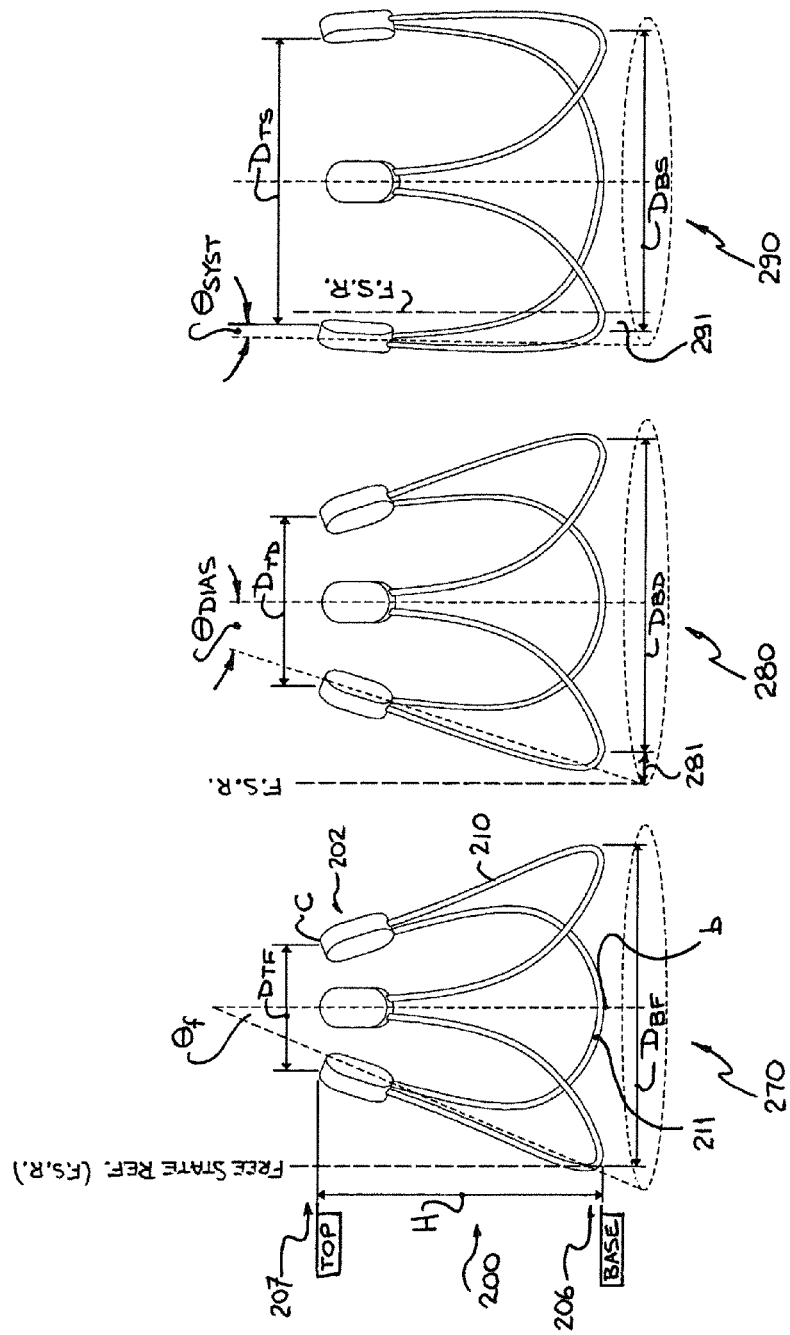
FIGS. 20A-20C, in an elevational side view, illustrate a prosthetic ring according to the present invention, and more specifically the wire frame structure thereof, respectively in a free-state non-implanted configuration, a first implanted ring configuration occurring at a time interval during the diastolic phase of the cardiac cycle, and a second implanted ring configuration occurring at a time interval during the systolic phase of the cardiac cycle, the mating anatomic structures not being shown.

Referring now to FIG. 20A, ring 1 is illustrated in its non-implanted free-state configuration 270, that is, in its fabricated configuration free from exposure to aortic pressure and cardiac muscle contractions. Elements of ring 1 such as annulus-restraining means 400 in nature of tether 401, elastomeric layer or sheath 500, and textile or fabric covering 600 are not shown in FIGS. 20A-20C to more clearly show the underlying three peak ring structure or frame 200.

In its free-state configuration 270, ring 1 has a shape that generally conforms to a truncated cone defined by a half cone angle $\theta_f$. Ring 1 is defined by a diameter $D_{BF}$ at its ring base 206, said diameter $D_{BF}$ being located substantially within plane BASE. At the top 207 of ring 1, said ring is defined by a smaller diameter $D_{TF}$, said smaller diameter $D_{TF}$ being located substantially within plane TOP. Plane TOP is located at a height H above plane BASE.

In proximity to ring base 206, the three trough sections 201 (and more specifically three points "b" located thereon) are spaced apart and define a diameter $D_{BF}$. In proximity to top 207 of ring 1, the three crest sections 202 (and points "c" located thereon) are spaced apart and define a diameter $D_{TF}$.

When ring 1 is implanted around aortic root 91 and exposed to cardiac muscle contractions and aortic pressures, it will deflect from its free state configuration to assume a variety of implanted configurations based on the variable or dynamic ring loading imparted from a varying cardiac cycle. According to the principles of the present invention, ring 1 is by virtue of its design configured and sized to deflect predetermined calculated amounts under said variable cardiac cycle, and as such assume a variety of advantageous implanted configurations that will allow ring 1 to modulate and control key aortic root dimensions. As a result, normal aortic valve physiology tends to be preserved or restored, as well as proper leaflet 912 coaptation and blood transport through the aortic valve 94.

Referring now to FIGS. 20B and 20C, two such advantageous implanted ring configurations are described in greater detail. FIG. 20B illustrates prosthetic ring 1 in an implanted first ring configuration 280, said first ring configuration occurring at a time interval during the diastolic phase of the cardiac cycle. In said first diastolic configuration, ring 1 still assumes a truncated cone or substantially conical shape, but the half cone angle $\theta_{DIAS}$ is smaller than $\theta_f$. Due largely to muscle contraction, the base diameter $D_{BD}$ is drawn radially inward relative to free state diameter $D_{BF}$, such radially inward ring deflection 281 being allowed to occur, substantially without restraint, by the design of tether member 401. Due to the aortic pressure loading now acting on ring 1 when said ring is exposed to the diastolic phase in the cardiac cycle, crest sections 202 are drawn apart relative to their free state configuration, to define a larger top diameter $D_{TD}$. Ring 1 is designed such that under diastolic pressure loading, crest sections 202 move apart relative to their free state configuration, but only to a predetermined extent that promotes proper valve leaflet coaptation.

FIG. 20C illustrates prosthetic ring 1 in an implanted second ring configuration 290 occurring at a time interval during the systolic phase of the cardiac cycle. In said second systolic configuration, ring 1 assumes a substantially cylindrical shape, with the half cone angle $\theta_{SYST}$ approaching zero. Due largely to heart muscle contraction at the onset of systole being overtaken by the resulting increase in ventricular and aortic pressure, the base diameter $D_{BS}$ is drawn radially outward relative to first diastolic diameter $D_{BD}$, such radially outward ring deflection 291 being permitted, regulated, and limited to a predetermined maximum by the design of tether member 401. Due to the increased aortic pressure loading now acting on ring 1 when said ring is exposed to the systolic phase in the cardiac cycle, crest sections 202 are drawn apart relative to their diastolic configuration, to define a larger top diameter $D_{TS}$. Ring 1 is designed in such a manner that under systolic conditions, trough sections 201 (and more specifically base portions 208 thereof) move apart to a predetermined maximum as governed or controlled by tether 401, and crest sections 202 move further apart relative to their diastolic configuration, but only to the predetermined extent that allows desired leaflet triangulation generally without overstressing of said leaflets.

According to the present invention, ring 1 is movable between a first diastolic configuration 280 where it assumes a substantially conical shape and a second systolic configuration 290 when it assumes a substantially cylindrical shape, the diameter at ring base 206 increasing in size from said diastolic to said systolic configuration and the diameter at ring top 207 increasing in size from said diastolic to said systolic configuration. Variants of ring 1 are possible without departing from the spirit of the invention. For instance, the diameter at base 206 of ring 1 may alternatively be designed to change very little, or remain substantially unchanged between the diastolic and systolic configuration, while only the diameter at top 207 increases in size between said diastolic and systolic configuration.

In a specific example of an embodiment according to the principles of the present invention, ring 1 may have the following dimensions in its free state configuration 270: $D_{BF}$=28 mm; H=19 mm; $D_{TF}$=14 mm; $\theta_f$=approx 20 degrees. In a diastolic configuration 280, the following dimensions: $D_{BD}$=25.5 mm; $D_{TD}$=18.8 mm; $\theta_{DIAS}$=approx 10 degrees. In a systolic configuration 290, the following dimensions: $D_{BS}$=31 mm; $D_{TS}$=29.2; $\theta_{SYST}$=approx 2.5 degrees.

It should be understood that this above example is just one specific example of a ring 1 embodiment, whose dimensions are determined in large part by the material properties of the ring components, and associated design of said ring components using said material properties. Different materials or designs may result in a ring geometry with different dimensions to the above example. For example, a second ring may be designed with a larger free state base diameter $D_{BF}$, but said second ring may still be designed to assume the same desired base diameter $D_{BS}$ in systolic configuration 290 as the first ring 1 in the above example. As such, this second ring will have a smaller deflection range between its free state configuration 270 and its systolic configuration 290, but a corresponding larger deflection range between its free state configuration 270 and its diastolic configuration 280.

Many other examples of prosthetic rings 1 may be designed without departing from the spirit of the present invention. Such other rings may have dimensions generally within the following range: $\theta_f$=10-20 degrees; H=0.6 $D_{BF}$ to 1.1 $D_{BF}$; $\theta_{DIAS}$=5-15 degrees; $\theta_{SYST}$=−5 to +5 degrees. In another example still, prosthetic ring 1 may have the following dimensions in its free state configuration 270: $D_{BF}$=30 mm; H=21 mm; $D_{TF}$=15 mm; $\theta_f$=approx 20 degrees. In a diastolic configuration 280, the following dimensions: $D_{BD}$=31.5 mm; $D_{TD}$=26 mm; $\theta_{DIAS}$=approx 7 degrees. In a systolic configuration 290, the following dimensions: $D_{BS}$=30.8 mm; $D_{TS}$=30 mm; $\theta_{SYST}$=approx 1 degree.

The range of H described above allows points "c" on ring 1 (and more specifically on crest sections 202 thereof) to be located either below points "C" on commissures 96, in register or close proximity to points "C", or above points "C". In the preferred embodiment of ring 1, H is preferably approximately 0.7-0.9 times the diameter of ring base 206 so that ring crest sections 202 are in general proximity to valve commissures 96. Variants of ring 1 may be configured with a variety of different heights H, for a given diameter of ring base 206, provided the proper ratio of top diameter 207 as a function of such varying height H is respected. For example, the greater the height H of a ring 1 for a given base diameter, the smaller the ratio of top diameter to base diameter of ring, and the greater the range of radial deflection or excursion of crest section 202 during the cardiac cycle, in order to promote adequate leaflet 912 coaptation during diastole, and desired triangulation of leaflets during systole to promote efficient blood transport through aortic valve 94. For a given base 206 diameter of ring 1, a greater ring height H may also have an impact on the placement of ring fixation sutures or method of attachment of ring 1 to aortic root 91.

Rings 1 with a preferred range of dimensions will lie in close proximity to valve annulus 92, and fixation sutures will tend to be placed from below valve leaflet 912 through said valve annulus, and subsequently through a portion of ring 1 in a manner to secure said ring to aortic root 91. In a ring 1 having a greater height H to ring base 206 diameter ratio, the base or inferior portion 208 or trough section 201 will still tend to be in close proximity to valve annulus 92 and allow fixation sutures to be placed below leaflet 912 in order to pierce said valve annulus and subsequently ring 1. However, in such higher rings, in parts of ring 1 approaching top 207 of said ring, such as crest section 202, fixation sutures may have to be placed above leaflet 912 in order to pierce through annulus 92 and subsequently through said higher lying ring portions. This is especially true when top 207 of ring 1 extends above the plane containing valve commissures 96.

For a given patient, the size of ring 1 to be implanted may be advantageously selected as a function of the native leaflet size and corresponding diastolic diameter required for adequate leaflet coaption, and extrapolating from such diastolic diameter the maximum ring base diameter required to properly resize a dilated aortic root or valve annulus.

Asymmetric variants of ring 1 may also be advantageously configured to cater for patients having unequally-sized native valve leaflets. For example, a variant asymmetric ring 1 may be configured with one or all of the three U-shaped trough sections 201 being of a different size. As such, the circumferential distance between adjacent crest sections 202 will be different. Alternatively still, ring 1 may be configured with one or all of crest sections 202 extending a different height above plane BASE, and one or all of trough sections 201 extending below base plane BASE.

Figure 21A:
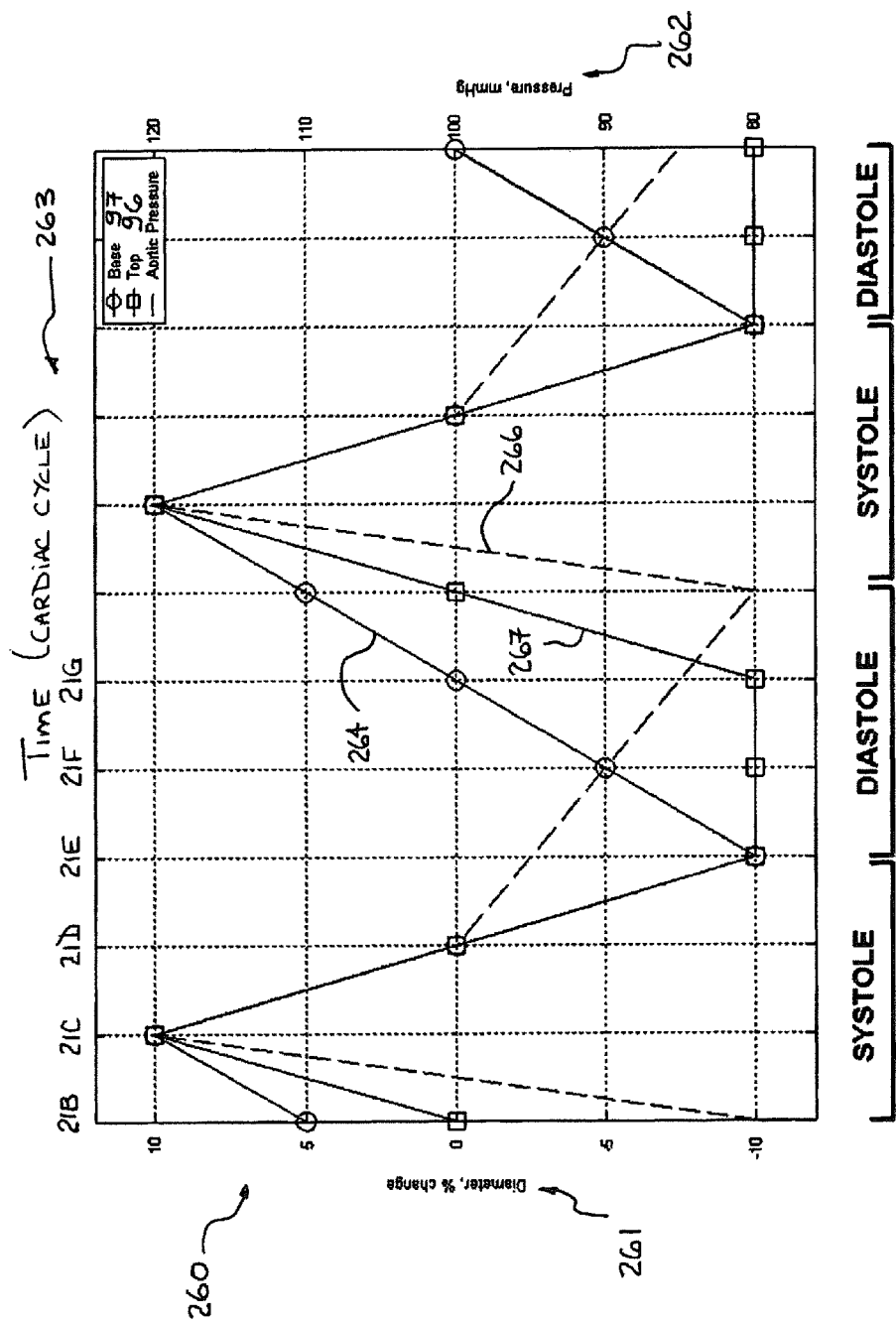
FIG. 21A, in a graphical view, illustrates the varying dimensions of a dynamic aortic root as a function of the different phases of the cardiac cycle.

Referring now to FIG. 21A, in a graphical representation 260 are illustrated the varying dimensions of a dynamic aortic root 90 as a function of the different phases of the cardiac cycle. Left vertical axis 261 of graph 260 plots the effective diameter of aortic root as a percentage change relative to a baseline diameter, said baseline diameter arbitrarily selected as the aortic root diameter at 100 mmHg of blood pressure. Right vertical axis 262 plots the blood pressure within the aortic root 90. Horizontal axis 263 plots time during the cardiac cycle, and in particular time points 21B, 21C, 21D occurring during the systolic phase, and time points 21E, 21F, 21G occurring during the diastolic phase. Although time point 21B to 21G are equally spaced along time axis 263, the time elapsed between two adjacent time points is not equal in duration. Plot 264 illustrates the variation in base diameter 97 of said aortic root as a function of time in the cardiac cycle, while plot 265 illustrates the variation in the top diameter of said aortic root, generally at the level of commissures 96. Plot 266 illustrates the variations in blood pressure within the aorta. FIG. 21A is based on data from a review of the medical literature focusing on aortic root dynamics, and diagrammatically illustrates a simplified interpretation of said data. Inclusion of new data or exclusion of some data may also alter the shape of the graphical plots in graph 260. As illustrated, the base diameter 97 and top diameter at level of commissures 96 vary +/-10 degrees relative to their baseline diameters.

FIGS. 21B-21G schematically represent a range of varying implanted ring configurations that ring 1 may assume during the different phases of the cardiac cycle. More specifically, FIGS. 21B, 21C, and 21D illustrate variations in ring 1 configuration occurring at three time points 21B, 21C, 21D occurring during the systolic phase, and FIGS. 21E, 21F, 21G occurring at three time points during the diastolic phase. In FIGS. 21B-21G, dashed line 267 represents a reference baseline diameter for ring 1, dotted line 268 represents a minimum diameter reference, typically inferior to baseline diameter by 10%, and dotted line 269 represents a maximum diameter reference, typically superior to baseline diameter by 10%. Not all of said lines are visible in each of said figures. As illustrated in FIG. 21F, ring 1 assumes a first diastolic configuration 280 with ring base 206 having a diameter of −5% relative to baseline 267, and ring top 207 having a diameter −10% relative to baseline 267. Said base and top diameters will vary with cardiac cycle and, as illustrated in FIG. 21C, ring 1 assumes a second systolic configuration 290 with ring base 206 and ring top 207 both having a diameter of +10% relative to baseline 267. Between said first and second configurations, ring 1 will vary in shape between a substantially conical shape at time point 21F and a substantially cylindrical shape at time point 21C.

Ring deflections at the top 207 of ring 1 are influenced in large part by the pressures within the aorta. Ring deflections at the base 206 of ring 1 are influenced mostly by muscle contractions and relaxations during the cardiac cycle, and are governed by the effect of annulus-restraining member or tether 401 which also sets a limit on the maximum base deflections and base diameter that ring 1 will be capable of assuming. Since the crest sections 202 of the ring 1 extend from the ring base 206, ring deflections at the base 206 also play a role in influencing ring deflections at the top 207 of ring 1. A prosthetic ring 1 according to the present invention is based on these and other design considerations to obtain the predetermined desired ring deflections. It is also understood that changing plots 261, 262 (either by design or to reflect alternate ways of interpreting the medical data) may result in a ring having different properties than the example illustrated in FIGS. 21B to 21G, and such a ring may have different changes in dimensions relative to baseline diameter 267.

Referring now more specifically to FIG. 22A, there is shown a composite prosthetic ring-conduit 6 in accordance with a sixth embodiment of the present invention. The embodiment 6 includes a prosthetic ring 8, substantially similar to any of the previously described prosthetic ring embodiments 1, 2, 3, 4, 5 and also includes a prosthetic conduit 7 that is advantageously attached to said ring 8 to form a composite ring-conduit 6 assembly.

Prosthetic conduit 7 is comprised of two sections or lengths of crimped fabric or textile, such as Dacron, or other biocompatible fabrics available with pleats and appropriate for implant use. A first conduit length or portion 71 is configured with pleats 711 in an axially stacked arrangement to allow stretch or substantially elastic expansion in an axial direction 713, thereby allowing said first conduit portion 71 to vary in length along said direction 713. As with commercially available conduits having axially-stacked pleats, the conduit is stretchable or expansible in an axial direction, but substantially non-elastic or non-expansible in the radial direction. A second conduit length or portion 72 is configured with pleats 721 in a circumferentially stacked arrangement to allow stretch of substantially elastic expansion in a circumferential direction 723, thereby allowing second conduit portion 72 to vary in diameter. As such, second conduit portion 72 is substantially non-expansible in the axial direction.

Conduit portion 72 is provided with sufficient pleating to permit ring 8 to expand or radially deflect within its plane TOP, and more specifically at points "c" thereon, according to the principles of the present invention as having been already described above in reference to FIGS. 19-21. Said sufficient pleating will permit ring 8 to assume its maximum ring diameter within plane TOP, substantially without any restraint being applied by said conduit portion 72 thereon.

The amount of expansion or contraction that conduit portion 72 (and pleats 721 thereof) will experience in proximity to the base plane BASE of ring 8 will be determined and controlled by the deflections of ring base 206 as governed by the effect of tether 401. That is, ring 8 will outwardly deflect or expand to assume a larger ring base diameter to the limit permitted by tether 401, while pleats 712 simultaneously unfold to allow said outward deflection substantially without hindrance or restraint thereon. Said expansion of ring 8 is being governed by the restraining or limiting effect of said tether and not by pleats 721 in conduit 72. Inward deflections or contractions of ring 8 may occur substantially freely since pleats 721 will adequately generally comply with ring deflections in a radially inward direction.

At conduit junction 722 between conduit portion 71 and 72, the axially stacked pleat 711 inhibits the radial expansion of circumferentially stacked pleats 721 of conduit portion 72. As such, length L of conduit portion 72 must be sufficiently long so that length G between TOP of ring 8 and conduit junction 722 provides sufficient allowance for points "c" on ring 8 to deflect radially, without being hindered or restrained by conduit portion 72 (or pleats 721 thereof). Typically, length G is approximately between 25% and 50% of length L. The stretch along direction 713 available in conduit portion 71 will allow for changes in length L that may result when points "c" deflect radially outward with the expansion of ring 8.

Circumferential pleats 721 also advantageously allow the creation of pseudo-sinuses of Valsalva 724, since conduit portion 72 is free to bulge outward in cusp region 203 from the effect of aortic pressure therewithin, and the unfolding of circumferentially stacked pleats 721. This bulging occurs even when ring 8 is in its first or diastolic configuration 280, and native valve leaflets 912 are coapting. As such, the normal physiology of aortic valve 94 tends to be preserved or restored.

Referring now more specifically to FIG. 22B, there is shown a variant composite prosthetic ring-conduit 60. Variant ring-conduit 60 is different to the ring-conduit 6 (FIG. 22A) in that it includes a variant prosthetic conduit 73, said conduit 73 however is still advantageously attached to ring 8 to form a composite ring-conduit assembly. Conduit 73 is similar in construction to a traditional aortic graft prosthesis with axially-stacked pleats 731. The diameter 732 of the conduit 73 is oversized relative to the aortic root base 97 diameter or valve annulus 92 diameter. Diameter 732 is also oversized relative to the maximum diameter that ring base 206 of ring 8 will assume during the different phases of the cardiac cycle. As such, oversized conduit 73 provides the material allowance to permit ring 8 to radially deflect or expand according to the principles of the present invention, said ring deflections being substantially unhindered by said oversized conduit. In accordance with the principles of the present invention, the maximum ring deflections at ring base 206 are governed or limited by the effect of tether 401. As such, ring 8 controls or modulates the dimensions of aortic root 91 (and also valve annulus 92 therewithin), independently from oversized conduit 73.

As a further variant to the composite prosthetic ring-conduit shown in FIGS. 22A and 22B, the pleated or crimped Dacron used for the conduit construction may be replaced by other similar biocompatible materials suitable for implant use and which allow for elastic expansion in one or more directions.

Referring now more specifically to FIG. 22C, there is shown a variant composite prosthetic ring-conduit 61 to the sixth embodiment illustrated in FIG. 22A. Variant ring-conduit 61 is different to the ring-conduit 6 in that it includes a variant prosthetic conduit 74, said conduit 74 however is still advantageously attached or integral with ring 81 to form a composite ring-conduit assembly 61. Conduit 74 is constructed from a substantially elastic biomaterial such as a hydrogel, or any other like elastic biomaterial suitable for implant use and for contact with blood. More specifically, conduit 74 is preferably constructed from a cryogel polyvinyl alcohol (cPVA) having been cross-linked by repeat freeze-thaw cycles to obtain the desired elasticity, similar to native aortic root tissue. Typically, three to five such freeze-thaw cycles may be employed to construct a cPVA biomaterial with the desired representative material properties. Ring 81 is preferably introduced within a mold, having the negative cavity shape of the cPVA conduit 74, that is used to fabricate said conduit. As such, ring 81 may be coated or overmolded by cPVA material during the fabrication of said conduit 74, and is advantageously embedded within conduit 74 (ring 81 illustrated in dashed line). Ring 81 is similar to prosthetic rings described in previous embodiments of ring 1 but may not include all the features of said rings. Ring 81 will include at least a scalloped three-peak ring structure 200 and a tether 401 similar to those of previous embodiments. Alternatively, conduit 74 may be produced independently and subsequently attached to ring 81 to produce a composite prosthetic ring-conduit 61. Conduit 74 may preferably include a bulging section 75 at each of the cusp zones 203 to more closely simulate the sinuses of Valsalva in native aortic root 90.

Bulging section 75 may be designed to have thinner wall thicknesses than the ascending aorta section 76, since radial deflections of the conduit within this section 75 will be substantially governed by the ring 81 according to the principles of the present invention as described in reference to FIGS. 19-21. A conduit 74 that is fabricated from a cPVA material, or other like biomaterial, is substantially elastic in an axial direction 751 and radial direction 752. Optionally, fibre reinforcements may be introduced in the cPVA material during the fabrication process to tailor material properties to desired stiffness along a desired conduit direction. Optionally, the cPVA material may be produced with different number of freeze-thaw cycles at different locations within conduit 74. As such, the material properties may be tailored at different conduit locations as a function of the number of freeze-thaw cycles. Alternatively, hydrogels that are cross-linked by a variety of methods (i.e., light, chemical, radiofrequency, etc.) may also be used instead of cPVA, provided such hydrogels are biocompatible, suitable for implant use in a blood-contacting environment, and preferably impervious to blood. Other examples of suitable conduit materials include polyurethane, polyetherurethaneurea, poly(carbonate)urethane, and other like materials or derivatives thereof.

The embodiments described and illustrated in FIGS. 22A-22C are preferably surgically implanted over a resected and scalloped aortic root 91 as shown in FIG. 3A. The embodiments described and illustrated in FIGS. 22A-22C provide a one-piece aortic root prosthesis that may advantageously be implanted as a single implantable structure 6, 60, 61, said implantable structure consisting of a prosthetic ring 8, 81 and an associated aortic conduit 7, 73, 74. Such a single structure 6, 60, 61 further facilitates an aortic valve-sparing procedure, or aortic root reconstruction, relative to a two-piece arrangement consisting of a separate prosthetic ring 1 and a separate independent aortic conduit being connected in-situ during said surgical procedure.

Figure 23C:
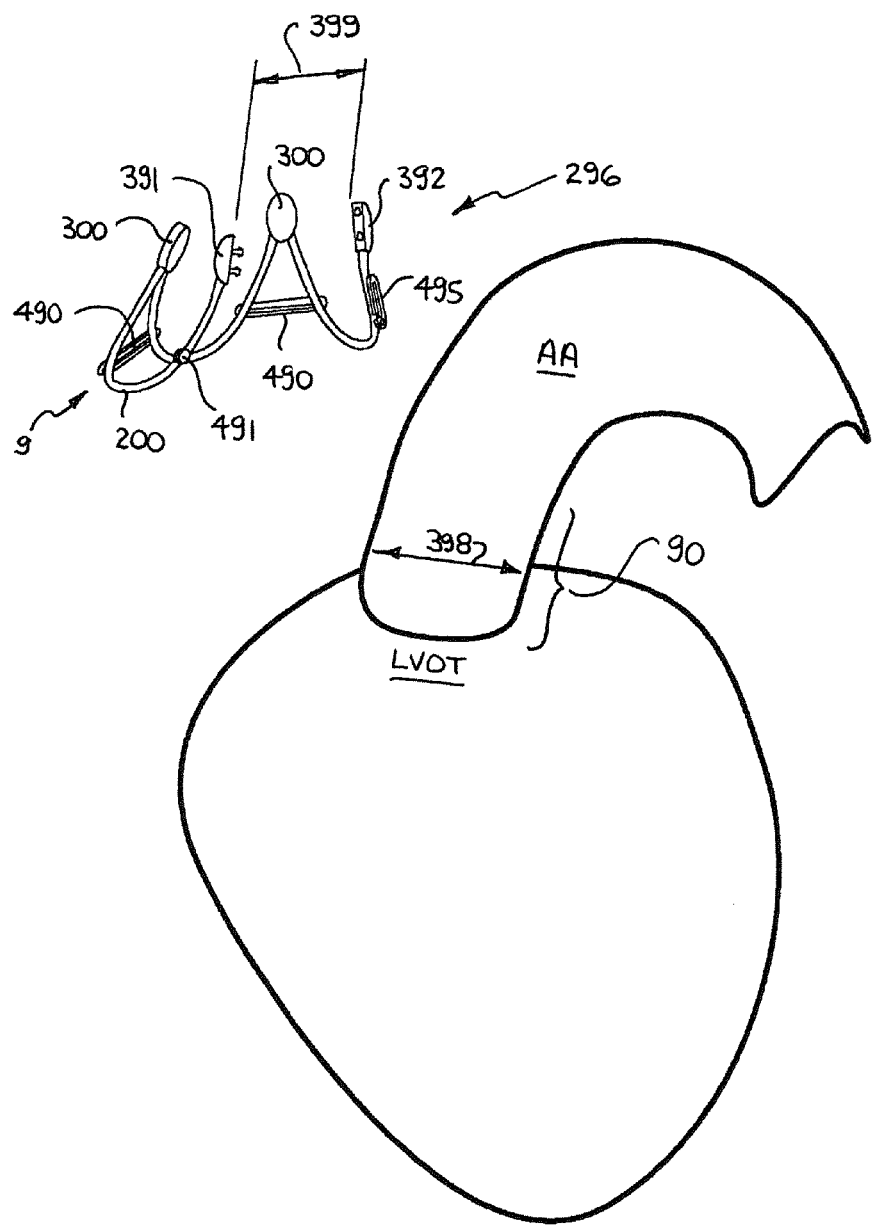

Referring now more specifically to FIGS. 23A-23C, there is shown a demountable prosthetic ring 9 in accordance with a seventh embodiment of the present invention. Ring 9 has a number of substantially similar features or components to ring 1, hence, similar reference numerals will be used to denote similar components. The main difference between rings 1 and 9 is that ring 9 is designed and configured to be deployed in a valve-sparing procedure, or aortic root reconstruction, avoiding the need to incise the aorta AA in order to allow placement of said ring 9 therearound.

As illustrated in FIGS. 23A-23C, some of the features or components that ring 9 has in common with ring 1 have not been shown in order to better illustrate the differences relative to ring 9. For instance, elastomeric sheath 500 and textile covering 600 have not been shown, but may be included as components of ring 9.

Ring 9 is comprised of three U-shaped frame members 210. At two of the three crest sections 202, two adjacent frame members 210 are connected by an end fitting 300, in a similar manner to previously described ring 1. At the remaining one of three crest sections 202, a two-piece assemblable end fitting 390 is used to close and complete said third crest section. End fitting 390 is comprised of two mating fittings 391, 392. Each of said mating fittings 391, 392 is attached to one of two remaining adjacent posts 212, in a similar manner as end fitting 300 is attached to posts 212. Fitting 391 is configured with pins 393 to provide a mating snap-fit engagement with cooperating holes 394 in mating fitting 392. Through engagement of mating fittings 391, 392, prosthetic ring 9 may assume a closed ring configuration 295 as illustrated in FIG. 23B, said closed ring configuration 295 being similar to ring 1. Variants to the pin-in-hole mechanical connection are possible such as tongue-in-groove, or any other mechanical connection that provides quick, reliable, assemblable connection of mating fittings 391, 392.

Proximal to base 206 of ring 9, each of said three frame members 210 is coupled to the other two adjacent members 210 by an annulus-limiting means or annulus-restraining member in the nature of brace or tie members 490, 495. Brace member 495 is demountably coupled to one of frame members 210, such that when said mating fittings 391, 392 are not connected and brace member 495 is uncoupled to member 210, ring 9 may assume an open ring configuration 296 as illustrated in FIG. 23C. In said open configuration, mating fittings 391, 392 may be sufficiently spaced apart by a gap 399 to allow ring 9 to be assembled around aortic root 90 without having to incise aorta AA. This is particularly advantageous since avoiding an aortotomy incision may also avoid placing the patient on extracorporeal circulation during the surgical procedure.

Three hinge-type pin members 492 and three translating pins 491 are circumferentially disposed around the base 206 of ring 9. Two translating pins 491 are attached to trough section 201 of one of the U-shaped frame members 210; two hinge pins 492 are attached to another one of the U-shaped members 210; and one of each pins 491, 492 are attached to the remaining one of the U-shaped members 210. Three generally elongate brace members 490, 495 are each pivotingly engaged or connected to one of said hinge pins 492. Brace members 490 are also slidingly engaged with a respective one of said translating pins 491 through a generally elongate slot 493 configured in said brace member 490, such sliding engagement being non-demountable. Conversely, brace member 495 is slidingly engaged with translating pin 491 through slot 497, with said sliding engagement being demountable through access groove 496.

In the assembled closed ring configuration 295 (FIG. 23B) said brace members 490, 495 span the infra-commissure zone 204, and translating pin 491 is located in its generally distal-most position relative to hinge-pin 492. A tangential or circumferential clearance 499 between pin 491 and terminal end 498 of slot 493 allows ring 9 to deflect at its base 206 without being affected by brace 490, 495. Over a predetermined range established by said circumferential clearance, said base of ring 9 can undergo radial deflections without being controlled or modulated by brace 490, 495. Beyond the limits of said predetermined range, pin 491 comes into contact with one of the extremities of said slot 493, 497 and as such the ring base 206 (and aortic root 90 attached thereto) is restrained or limited from further radial deflections. Braces 490, 495 restrain ring 9 from further radially outward movement, to the extent that brace flexibility will allow, contingent on the design and material of said brace. For example, a very stiff brace can entirely prevent further radially outward deflections, while an elastic brace will restrain further deflections to the degree that its structural stiffness will permit. Brace 490, 495 may be fabricated from a metallic, or polymeric material. Pins 491, 492 are preferably attached to, and protruding from, frame member 210.

With mating fittings 391, 392 not connected, and with brace 495 decoupled from pin 491, ring 9 may be folded or collapsed to assume a compact, collapsed configuration 294 as illustrated in FIG. 23A. Pivoting of brace members 490, 495 about hinge pin 492 will urge pins 491 to translate along slot 493 toward pins 492. In the limit condition, when said pins 491 are in general proximity to hinge pins 492, ring 9 is in its most compact configuration with brace members 490, 495 being substantially aligned with posts 212. Such a compact arrangement 294 allows ring 9 to be advantageously deployed through an endoscopic or intercostal port-access surgical approach. As such, a classic sternotomy incision may be avoided.

FIGS. 24A-24D illustrate a variety of suturing arrangements and methods in which a prosthetic ring 1, 2, 3, 4, 5 may be implanted on a resected aortic root 91, and affixed to a vascular conduit 95.

FIG. 24A illustrates a suturing arrangement including two suture lines 901 and 902. In this arrangement, fringe 910 of aortic root tissue lies outboard relative to vascular conduit 95. Suture 901 is placed above leaflet 912 and attaches fringe 910 to conduit 95. Suture 902 is placed below the leaflet 912, through the native valve annulus 92 and through prosthetic ring 1.

FIG. 24B illustrates a suturing arrangement including one suture line 903 having two surgical needles 904 (double armed). In this arrangement, fringe 910 also lies outboard relative to vascular conduit 95. One end of suture 903 is placed from above leaflet 912, through valve annulus 92 and through prosthetic ring 1. The opposed end of suture 903 is placed through vascular conduit 95 and through fringe 910. The two ends of suture 903 are then tied outside the aorta.

FIG. 24C illustrates a suturing arrangement including one suture line 903 having two surgical needles 904 (double armed). In this arrangement, fringe 910 of aortic root tissue lies inboard relative to vascular conduit 95. One end of suture 903 is placed from above leaflet 912, through valve annulus 92 and through prosthetic ring 1. The opposed end of suture 903 is placed through fringe 910 and vascular conduit 95. The two ends of suture 903 are then tied outside the aorta.

FIG. 24D illustrates a suturing arrangement including one suture line 903 having two surgical needles 904 (double armed). In this arrangement, fringe 910 of aortic root tissue lies inboard relative to vascular conduit 95. One end of suture 903 is placed from below leaflet 912, through valve annulus 92 and through prosthetic ring 1. The opposed end of suture 903 is also placed from below leaflet through valve annulus 92 through fringe 910 and through vascular conduit 95. The two ends of suture 903 are then tied outside the aorta.

Figures 25A, 25B:
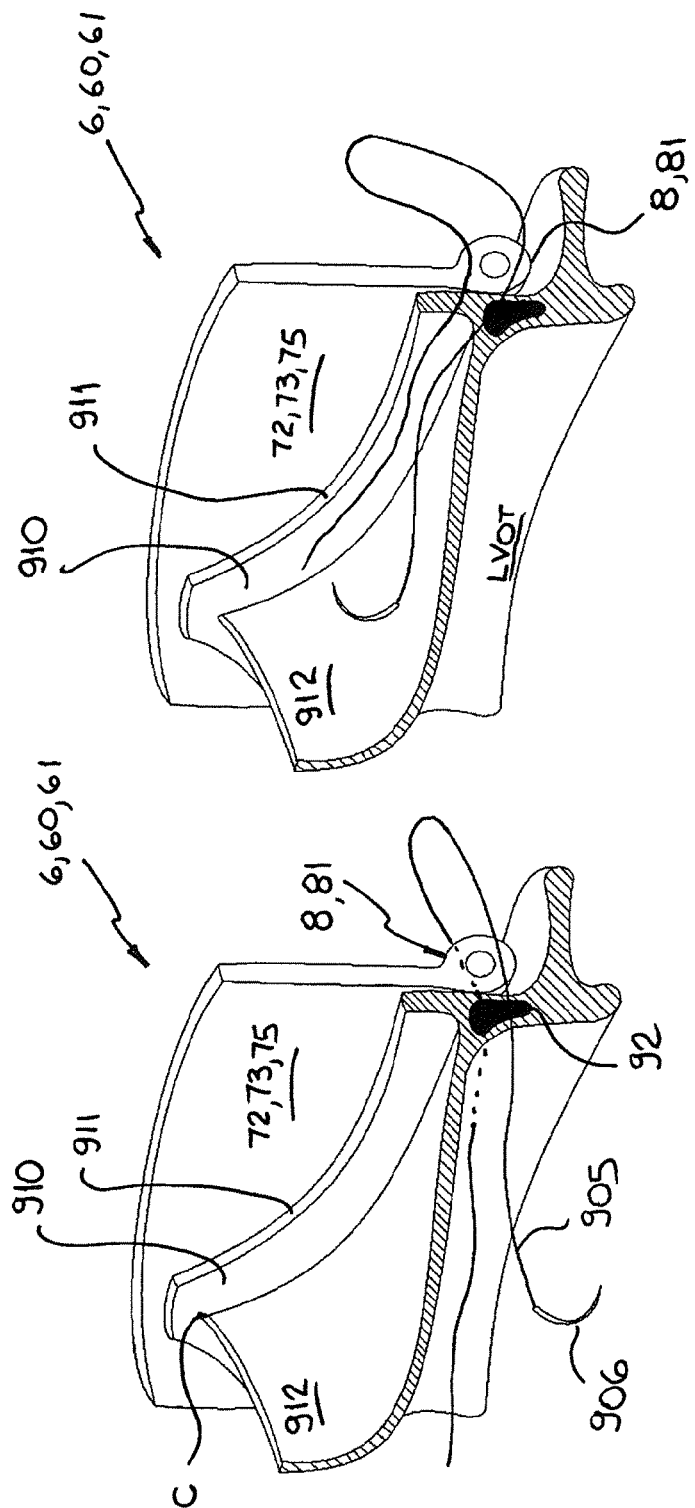
FIGS. 25A-25B, in a schematic cutaway view, illustrate variants for suturing the prosthetic ring and conduit arrangement shown in FIG. 22A to a scalloped aortic root portion similar to the one shown in FIG. 3A.
Figure 26A:
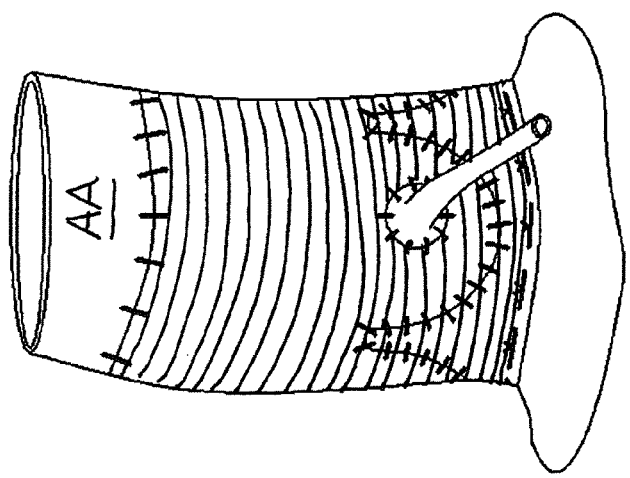
FIGS. 26A-26B, in a perspective elevational view, illustrate current surgical reconstructions of the aortic root as references, without the use of a prosthetic ring according to the present invention.
Figure 26B:
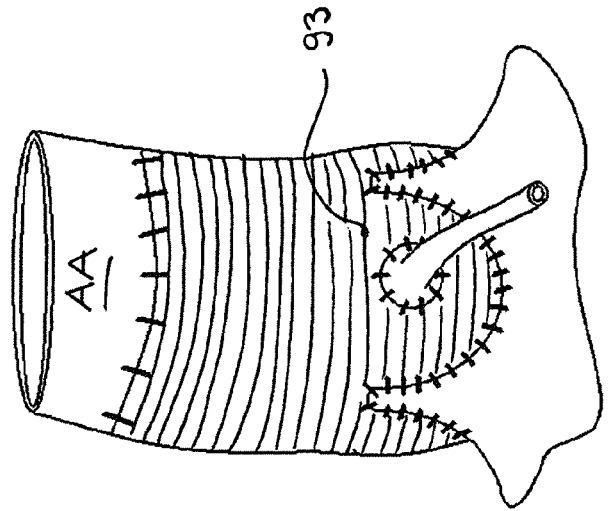

FIGS. 25A-25B illustrate a variety of suturing arrangements and method in which a composite prosthetic ring-conduit 6, 60, or 61 may be implanted on and affixed to a resected aortic root 91.

FIG. 25A illustrates a suturing arrangement including one suture line 905 having one surgical needle 906. In this arrangement, fringe 910 lies inboard relative to conduit section 72, 73 or 75. One end of suture 905 is placed from below leaflet 912, through valve annulus 92 and through prosthetic ring 8, 81. The same end of suture 905 is then returned through ring 8, 81 and through valve annulus 92. The two ends of suture 905 are then tied inside the aorta. Alternatively, one end of a double-armed suture is placed from below leaflet 912, through valve annulus 92 and through prosthetic ring 8, 81. The other end of double-armed suture is also placed from below leaflet 912, through valve annulus 92 and through prosthetic ring 8, 81 to create a U-stitch. The two ends of double-armed suture are then tied outside the aorta.

FIG. 25B illustrates a suturing arrangement including one suture line 905 having one surgical needle 906. In this arrangement, fringe 910 also lies inboard relative to conduit section 72, 73 or 75. One end of suture 905 is placed from above leaflet 912, through valve annulus 92 and through prosthetic ring 8, 81. The same end of suture 905 is then returned through ring 8, 81 and through fringe 910. The two ends of suture 905 are then tied inside the aorta.

In valve-sparing surgeries that do not involve resection of the aortic root to remove aneurysmal tissue, the suturing methods described above can be revised to exclude placement of sutures through the synthetic vascular conduit.

In association with the suturing methods for fixation of said prosthetic rings to said aortic root, various tether configurations may advantageously allow for the placement of ring positioning guide sutures therethrough to aid the surgeon in proper placement and anchoring of ring 1 relative to scalloped aortic root 91, or native aortic root 90.

Other suturing arrangements consisting of a combination of one or more of the above-described arrangements are also possible.

In the foregoing descriptions of the various ring embodiments, it is understood that a scalloped aortic root 91 and native aortic root 90 may be used interchangeably, depending on whether or not the valve sparing procedure involves resection of aortic tissue. The various ring embodiments are generally attached to a scalloped aortic root 91 when resection of aortic tissue is required, such as to remove aneurysmal aortic tissue. In such valve-sparing procedures, the use of a vascular conduit 95 (or ring-conduit 6, 60, 61) is also required to replace said resected aneurysmal tissue. In valve-sparing procedures that do not involve resection of a portion of the aorta or aortic root tissue, such as those procedures that treat aortic insufficiency or annulo-ectasia without aneurysm of the aortic root, the various ring embodiments are attached to a native aortic root 90 and the use of a vascular conduit 95 is generally not required.

In the foregoing descriptions of the various ring embodiments, when said ring or aortic root assumes a shape that is not perfectly circular in a given plane thereof, it is understood that references to the term "diameter", shall also mean changes to the perimeter of said ring or aortic root in said given plane, or changes to the area contained within said perimeter in said given plane.

In surgical procedures that make use of a vascular conduit 95, the various ring embodiments may first be attached to scalloped aortic root 91, and said vascular conduit subsequently attached, in situ, to connect the scalloped aortic root-ring interface to the native ascending aorta AA. Alternatively, vascular conduit 95 may first be attached to the scalloped aortic root 91 and the various ring embodiments subsequently attached to aortic root 91, in situ, before closure of the aortotomy incision between said vascular conduit 95 and ascending aorta AA.

A surgical method associated with the implant of ring 1 may include the following steps:

i. Resect aortic root above leaflet to leave scalloped fringe 910 (FIG. 3A);

ii. Assess condition and size of leaflets 912 to determine size of valve annulus required to correct aortic insufficiency and restore proper leaflet coaptation;

iii. Select appropriate size of ring 1 that will adequately resize dilated aortic root to ensure leaflet coaptation during diastole;

iv. Preferably, place three U-stitch sutures through each of inter-leaflet triangle 98 of aortic root 91 and corresponding infra-commissure zone 204 of ring 1 (preferably through tether 401), to serve as gross positioning sutures for ring 1;

v. Place an adequate number of ring fixation sutures (preferably U-stitches) through valve annulus 92 and U-shaped section 201 or crest section 202 of ring 1, for example one suture at each inferior most location 208 of trough section 201, and one suture through each of crest sections 202;

vi. Descend ring 1 onto scalloped aortic root 91 by sliding said ring over suture lines placed through ring 1 and aortic root 91;

vii. Assess leaflet coaptation in aortic root resized by ring 1;

viii. If leaflet coaptation is satisfactory, tie loose suture ends to securely fix ring 1 to aortic root 91;

ix. Tailor and fashion a tubular aortic conduit 95 with appropriately sized and configured scallops so that said conduit scallops approximate scallops of aortic fringe 910 and/or scallops or ring structure 200;

x. Suture conduit 95 to fringe 910 and/or ring 1 and to ascending aorta AA to re-establish blood flow.

In the event that a composite prosthetic ring-conduit 6, 60, or 61 is used, step ix is avoided, and step x is revised to include only suturing of ring-conduit 6, 60, or 61 to ascending aorta AA.

What is claimed is:

1. A device for the surgical repair of an aortic valve of a patient, the aortic valve defining a valve axis and contained within a generally tubular aortic root, the aortic valve including a plurality of valve leaflets connected to the aortic root, the leaflets each having a free margin portion movable as a function of the different phases of the cardiac cycle between a first leaflet position in which the aortic valve is exposed to a diastolic phase of the cardiac cycle and in which the leaflet free margins are in an approximated spatial relationship to restrict blood flow through the aortic valve and a second leaflet position in which the aortic valve is exposed to a systolic phase of the cardiac cycle and in which the leaflet free margins are in a spaced apart relationship to allow blood flow through the aortic valve, said device comprising:

an annular ring, said annular ring having a scalloped profile and being configured and sized for placement externally around said aortic root, said annular ring including three U-shaped members connected to each other at three crest fittings and arranged around a ring axis to form a closed-ring configuration, said U-shaped members each having a base portion and each having an upper portion adjacent said three crest fittings, said annular ring defining a first diameter proximate said base portion and constructed to allow circumferential movement of said base portions closer to one another such that said annular ring defines a second diameter proximate said base portion being smaller than said first diameter, one of said crest fittings being configured as a demountable crest fitting including two mating fitting members, said closed-ring configuration transformable into an open-ring configuration when said two mating fitting members are disassembled; and three annulus restraining brace members, wherein when said annular ring is in said closed-ring configuration each of said annulus restraining brace members extends between and couples a different pair of adjacent U-shaped members at a location proximate said base portions of said adjacent U-shaped members, one of said annulus restraining brace members being configured as a demountable brace member able to be decoupled from one of said U-shaped members in one of said pairs of adjacent U-shaped members in said open-ring configuration, said demountable annulus restraining brace member extending between the pair of adjacent U-shaped members joined at said upper portions by said demountable crest fitting;

whereby, in use, when said annular ring is in said closed-ring configuration, under influence of the different phases of the cardiac cycle, said annulus-restraining brace members are constructed to: 1) allow inward displacement of said base portions of said U-shaped members toward said ring axis, the inward displacement occurring over a predetermined range without being controlled or modulated by said annulus-restraining brace members and resulting in circumferential movement of said base portions of said U-shaped members closer to one another, and 2) limits maximum displacement of said base portions of said U-shaped members away from said ring axis in order to constrain the maximum size of the aortic root so as to promote coaptation of the leaflet free margins during the diastolic phase of the cardiac cycle.

2. The device of claim 1, wherein, in said open-ring configuration, said device is transformable into a compact, collapsed-ring configuration, said collapsed-ring configuration defined by a third diameter being smaller than said annular ring second diameter proximate said base portions of said U-shaped members.

3. The device of claim 2 wherein each of said three brace members is pivotingly connected to one of said U-shaped members in said different pair of adjacent U-shaped members, and slidingly coupled to the other said U-shaped member of said different pair of adjacent U-shaped members.

4. The device of claim 3 wherein each of said three brace members is provided with an elongate slot to allow said sliding coupling with said U-shaped members, and a hole to allow said pivoting connection with said U-shaped members.

\* \* \* \* \*